US008410077B2

(12) United States Patent
Antle

(10) Patent No.: US 8,410,077 B2
(45) Date of Patent: *Apr. 2, 2013

(54) SULFOALKYL ETHER CYCLODEXTRIN COMPOSITIONS

(75) Inventor: Vincent Antle, Olathe, KS (US)

(73) Assignee: CyDex Pharmaceuticals, Inc., La Jolla, CA (US)

(*) Notice: Subject to any disclaimer, the term of this patent is extended or adjusted under 35 U.S.C. 154(b) by 542 days.

This patent is subject to a terminal disclaimer.

(21) Appl. No.: 12/613,103

(22) Filed: Nov. 5, 2009

(65) Prior Publication Data
US 2010/0093663 A1 Apr. 15, 2010

Related U.S. Application Data

(63) Continuation of application No. 12/404,174, filed on Mar. 13, 2009, now Pat. No. 7,635,773.

(60) Provisional application No. 61/048,518, filed on Apr. 28, 2008.

(51) Int. Cl.
A61K 31/724 (2006.01)
C07H 15/04 (2006.01)

(52) U.S. Cl. ............. 514/54; 514/58; 536/120; 536/122

(58) Field of Classification Search .................. None
See application file for complete search history.

(56) References Cited

U.S. PATENT DOCUMENTS

| 3,426,011 | A | 2/1969 | Parmerter et al. |
| 4,738,923 | A | 4/1988 | Ammeraal |
| 4,920,214 | A | 4/1990 | Friedman |
| 5,134,127 | A | 7/1992 | Stella et al. |
| 5,376,645 | A | 12/1994 | Stella et al. |
| 5,393,880 | A | 2/1995 | Shieh et al. |
| 5,569,756 | A | 10/1996 | Qi et al. |
| 5,620,872 | A | 4/1997 | Shieh et al. |
| 5,874,418 | A | 2/1999 | Stella et al. |
| 5,935,941 | A | 8/1999 | Pitha |
| 6,033,573 | A | 3/2000 | Toles et al. |
| 6,046,177 | A | 4/2000 | Stella et al. |
| 6,153,746 | A | 11/2000 | Shah et al. |
| 6,337,302 | B1 | 1/2002 | Teng et al. |
| 7,034,013 | B2 | 4/2006 | Thompson et al. |
| 7,625,878 | B2 | 12/2009 | Stella et al. |
| 7,629,331 | B2 | 12/2009 | Pipkin et al. |
| 7,635,773 | B2 | 12/2009 | Antle |
| 2003/0055023 | A1 | 3/2003 | Rajewski et al. |
| 2005/0164986 | A1 | 7/2005 | Mosher et al. |
| 2006/0258537 | A1 | 11/2006 | Stella et al. |
| 2007/0175472 | A1 | 8/2007 | Pipkin et al. |
| 2009/0011037 | A1 | 1/2009 | Pipkin et al. |
| 2009/0123540 | A1 | 5/2009 | Pipkin et al. |

FOREIGN PATENT DOCUMENTS

| EP | 1950227 A1 | 7/2008 |
| WO | WO 91/11172 A1 | 8/1991 |
| WO | WO 02/055562 A2 | 7/2002 |
| WO | WO 2006/071491 A1 | 7/2006 |

OTHER PUBLICATIONS

Declaration under 37 CFR 1.132 by Vincent Antle, submitted Aug. 10, 2009 in U.S. Appl. No. 12/404,174.*
Betadex, *Pharmacopeial Forum* 34:127 (Jan.-Feb. 2008) The United States Pharmacopeial Convention.
Luna, E.A., "Fractionation and characterization of 4-sulfobutyl ether derivatives of cyclomaltoheptaose (β-cyclodextrin)," *Carbohydr. Res.* 299:103 (1997) Elsevier Science Ltd.
Stella, V.J., "SBE7-β-CD, A New, Novel and Safe Polyanionic β-Cyclodextrin Derivative: Characterization and Biomedical Applications," in *Proc. of the Eighth Int'l Symp. on Cyclodextrins*, Budapest, Hungary, Mar. 31-Apr. 2, 1996, Szejtli, J., and Szente, L., eds., pp. 471-476 (1996) Kluwer Academic Publishers, Dordrecht, NL.
Szente, L., "Highly soluble cyclodextrin derivatives: chemistry, properties, and trends in development," *Adv. Drug Delivery Rev.* 36:17 (1999) Elsevier Science Publishers, B.V.
International Search Report & Written Opinion for International Application No. PCT/US2009/02572, dated Jun. 15, 2009.
An original, executed Second Declaration of Dr. Vincent Antle Under 37 C.F.R. § 1.132, executed Aug. 12, 2009.
Office Action dated Jul. 8, 2009 in U.S. Appl. No. 12/404,174, U.S. Patent and Trademark Office, Alexandria, Virginia.
Accelerated Examination Support Document filed Mar. 13, 2009 in U.S. Appl. No. 12/404,174.
Declaration of Dr. Vincent Antle Under 37 C.F.R. § 1.132 filed Aug. 10, 2009 in U.S. Appl. No. 12/404,174.
Extended European Search Report dated Jul. 18, 2011 in European Application No. 09739150.2, European Patent Office, Munich, Germany.
"DARCO® KB-G" Product Datasheet, Norit Americas Inc., Marshall, Texas, United States (Jul. 2007).
Jacquet, R., et al., "Liquid chromatography analysis of monosubstituted sulfobutyl ether-β-cyclodextrin isomers on porous graphitic carbon," *J. Sep. Sci.* 27(14):1221-1228, Wiley-VCH Verlag GmbH & Co. KGaA, Weinheim, Germany (2004).
Sotthivirat, S., et al., "Evaluation of various properties of alternative salt forms of sulfobutylether-β-cyclodextrin, $(SBE)_{7M}$-β-CD," *Int. J. Pharm.* 330:73-81, Elsevier B.V., Amsterdam, Netherlands (2007).
Tongiani, S., et al., "Sulfoalkyl Ether-Alkyl Ether Cyclodextrin Derivatives, Their Synthesis, NMR Characterization, and Binding of 6α-Methylprednisolone," *J. Pharm. Sci.* 94(11):2380-2392, Wiley-Liss, Inc. and the American Pharmacists Association, United States (2005).

(Continued)

Primary Examiner — Eric S Olson
(74) Attorney, Agent, or Firm — Knobbe, Martens, Olson & Bear LLP

(57) ABSTRACT

SAE-CD compositions are provided, along with methods of making and using the same. The SAE-CD compositions comprise a sulfoalkyl ether cyclodextrin having an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

76 Claims, 5 Drawing Sheets

OTHER PUBLICATIONS

Wenz, G. &Höfler, T., "Synthesis of highly water-soluble cyclodextrin sulfonates by addition of hydrogen sulfite to cyclodextrin allylethers," *Carbohydr. Res. 322*:153-165, Elsevier Science Ltd., United Kingdom (1999).

Co-pending U.S. Appl. No. 13/243,956, filed Sep. 23, 2011, Not Yet Published.

Crowley et al., Drug-Excipient Interactions, Pharmaceutical Technology, Mar. 2001, pp. 1-6, Advanstar Publication.

EPO, Summons to Attend Oral Proceedings Pursuant to Rule 115(1) EPC, Feb. 8, 2013, for EPO Patent Application No. 09739150.2-1464, pp. 1-14.

Wichmann, Dr. Hendrik of Wuesthoff & Wuesthoff, Third Party Observations Pursuant to Article 115 EPC, Nov. 21, 2012, pp. 1-12.

* cited by examiner

SULFOALKYL ETHER CYCLODEXTRIN COMPOSITIONS

CROSS-REFERENCE TO RELATED APPLICATIONS

This application is a Continuation of U.S. application Ser. No. 12/404,174, filed Mar. 13, 2009, now U.S. Pat. No. 7,635,773, which claims the benefit of the filing date of U.S. Appl. No. 61/048,518, filed Apr. 28, 2008, both of which are incorporated by reference herein in their entireties.

BACKGROUND OF THE INVENTION

1. Field of the Invention

The present invention relates to compositions comprising sulfoalkyl ether cyclodextrin ("SAE-CD") compositions, and methods for preparing and using the same.

2. Background of the Invention

Sulfoalkyl ether cyclodextrin ("SAE-CD") derivatives are polyanionic, hydrophilic, water-soluble cyclodextrins derivatized with sulfoalkyl ether functional groups. An anionic sulfoalkyl ether substituent dramatically improves the aqueous solubility and safety compared to an underivatized cyclodextrin. Reversible, non-covalent, complexation of drugs with sulfoalkyl ether-substituted cyclodextrins generally allows for increased solubility of an active pharmaceutical ingredient and, in some cases, increased stability of drugs in aqueous solutions.

A sulfobutyl ether-β-cyclodextrin having an average degree of substitution of about seven (7) is currently marketed as CAPTISOL® (CyDex Pharmaceuticals, Inc., Lenexa, Kans.). CAPTISOL® has the following chemical structure:

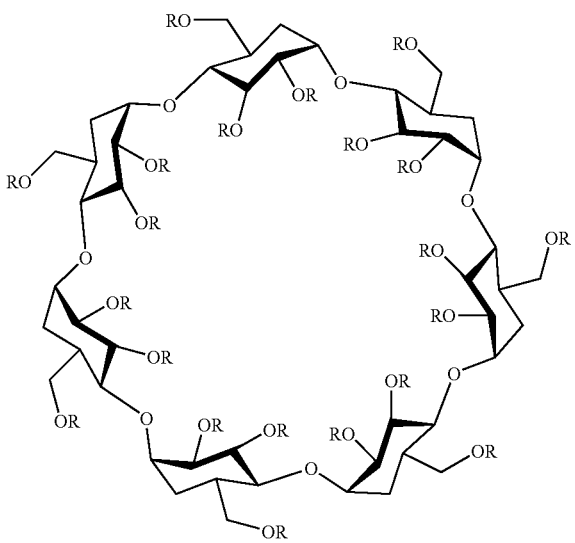

wherein R is $(-H)_{21-n}$ or $(-CH_2CH_2CH_2CH_2SO_3^-Na^+)_n$, and n is 6-7.1.

Sulfoalkyl ether-substituted cyclodextrins can be manufactured according to the processes disclosed in, e.g., U.S. Pat. Nos. 5,134,127, 5,376,645 and 6,153,746, which are herein incorporated by reference in their entirety. The SAE-CD derivatives or cyclodextrin derivatives containing a sulfonate functional group can also be made according to Parmerter et al. (U.S. Pat. No. 3,426,011); Gadelle et al. (U.S. Pat. No. 5,578,719); Joullié et al. (U.S. Pat. Nos. 5,760,015 and 5,846,954); Buchanan et al. (U.S. Pat. Nos. 6,610,671 and 6,479,467); Perrier et al. (U.S. Pat. No. 6,524,595); Uchiyama et al. (U.S. Pat. No. 5,512,665); Lammers et al., Recl. Trav. Chim. Pays-Bas 91:733 (1972); Staerke 23:167 (1971); Qu et al., J. Inclusion Phenom. Macro. Chem. 43:213 (2002); Yoshinaga, Japanese Patent No. JP 05001102; U.S. Pat. No. 5,241,059; PCT International Publication No. WO 01/40316, Adam et al., J. Med. Chem. 45:1806 (2002); and Tarver et al., Bioorg. Med. Chem. 10:1819 (2002).

Impurities present in a SAE-CD composition can thus reduce the shelf-life and potency of an active agent composition. Impurities can be removed from a cyclodextrin or SAE-CD composition by exposure to (e.g., mixing with) activated carbon. The treatment of cyclodextrin-containing aqueous solutions and suspensions with activated carbon is known. See, e.g., U.S. Pat. Nos. 4,738,923, 5,393,880 and 5,569,756. However, there is a continued need for SAE-CD compositions with higher purity.

BRIEF SUMMARY OF THE INVENTION

The present invention demonstrates that substantial removal of both a phosphate and a drug-degrading impurity from a SAE-CD composition provides a composition that can be readily mixed with an active agent to provide a high-stability formulation.

The present invention is directed to a SAE-CD composition comprising a sulfoalkyl ether cyclodextrin and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

The present invention is directed to a composition comprising an excipient and a SAE-CD composition, wherein the SAE-CD composition comprises a sulfoalkyl ether cyclodextrin and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

The present invention is directed to a composition comprising one or more active agents and a SAE-CD composition, wherein the SAE-CD composition comprises a sulfoalkyl ether cyclodextrin and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

In some embodiments, the SAE-CD composition has an absorption of less than 0.2 A.U. due to a color-forming agent, as determined by UV/vis spectrophotometry at a wavelength of 320 nm to 350 nm for an aqueous solution containing 500 mg of the SAE-CD composition per mL of solution in a cell having a 1 cm path length.

In some embodiments, the SAE-CD composition further comprises:
less than 20 ppm of a sulfoalkylating agent;
less than 0.5% wt. of an underivatized cyclodextrin;
less than 1% wt. of an alkali metal halide salt; and
less than 0.25% wt. of a hydrolyzed sulfoalkylating agent.

In some embodiments, the SAE-CD composition has an absorption of less than 0.5 A.U. due to a drug-degrading agent, as determined by UV/vis spectrophotometry at a wavelength of 245 nm to 270 nm for an aqueous solution containing 500 mg of the SAE-CD composition per mL of solution in a cell having a 1 cm path length.

In some embodiments, the sulfoalkyl ether cyclodextrin is a compound of Formula (1):

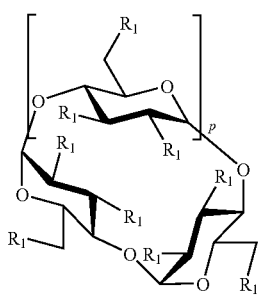

Formula (1)

wherein p is 4, 5 or 6, and $R_1$ is independently selected at each occurrence from —OH or -SAE-T; and wherein -SAE- is independently selected at each occurrence from a —O—($C_2$-$C_6$ alkylene)-$SO_3^-$ group, and -T is independently selected at each occurrence from pharmaceutically acceptable cations, provided that at least one $R_1$ is —OH and at least one $R_1$ is -SAE-T.

In some embodiments, -SAE- is a —O—($C_4$ alkylene)-$SO_3^-$ group at each occurrence, and -T is $Na^+$ at each occurrence.

In some embodiments, the SAE-CD composition comprises:
less than 50 ppm of a phosphate;
less than 10 ppm of a sulfoalkylating agent;
less than 0.2% wt. of an underivatized cyclodextrin;
less than 0.5% wt. of an alkali metal halide salt; and
less than 0.1% wt. of a hydrolyzed sulfoalkylating agent;
wherein the SAE-CD composition has an absorption of less than 0.5 A.U. due to the drug-degrading agent, as determined by UV/vis spectrophotometry at a wavelength of 245 nm to 270 nm for an aqueous solution containing 500 mg of the SAE-CD composition per mL of solution in a cell having a 1 cm path length; and
wherein the SAE-CD composition has an absorption of less than 0.2 A.U. due to the color-forming agent, as determined by UV/vis spectrophotometry at a wavelength of 320 nm to 350 nm for an aqueous solution containing 500 mg of the SAE-CD composition per mL of solution in a cell having a 1 cm path length.

In some embodiments, the SAE-CD composition comprises:
less than 10 ppm of a phosphate;
less than 2 ppm of a sulfoalkylating agent;
less than 0.1% wt. of an underivatized cyclodextrin;
less than 0.2% wt. of an alkali metal halide salt; and
less than 0.08% wt. of a hydrolyzed sulfoalkylating agent;
wherein the SAE-CD composition has an absorption of less than 0.25 A.U. due to the drug-degrading agent, as determined by UV/vis spectrophotometry at a wavelength of 245 nm to 270 nm for an aqueous solution containing 500 mg of the SAE-CD composition per mL of solution in a cell having a 1 cm path length; and
wherein the SAE-CD composition has an absorption of less than 0.1 A.U. due to the color-forming agent, as determined by UV/vis spectrophotometry at a wavelength of 320 nm to 350 nm for an aqueous solution containing 500 mg of the SAE-CD composition per mL of solution in a cell having a 1 cm path length.

In some embodiments, the SAE-CD composition comprises:
less than 5 ppm of a phosphate;
less than 2 ppm of a sulfoalkylating agent;
less than 0.1% wt. of an alkali metal halide salt; and
less than 0.05% wt. of a hydrolyzed sulfoalkylating agent.

The present invention is also directed to a composition comprising an excipient and a SAE-CD composition, wherein the SAE-CD composition comprises a sulfobutyl ether cyclodextrin having an average degree of substitution of 7 and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 500 mg of the SAE-CD composition per mL of solution in a cell having a 1 cm path length.

The present invention is also directed to a composition comprising one or more active agents and a SAE-CD composition, wherein the SAE-CD composition comprises a sulfobutyl ether cyclodextrin having an average degree of substitution of 7 and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 500 mg of the SAE-CD composition per mL of solution in a cell having a 1 cm path length.

In some embodiments, a SAE-CD composition can comprise:
less than about 250 ppb of sulfoalkylating agent;
less than about 0.1% wt., less than 0.08% wt., or less than 0.5% wt. of underivatized cyclodextrin;
less than 200 ppm, less than 150 ppm, less than 100 ppm, less than 50 ppm, 20 ppm, less than 10 ppm, less than 5 ppm, or less than 2 ppm of phosphate;
less than 1% wt., less than 0.5% wt., less than 0.2% wt., less than, 0.1% wt., less than, 0.08% wt., or less than, 0.05% wt. of alkali metal halide salt;
less than 1% wt., less than 0.5% wt., less than 0.25% wt., less than 0.1% wt., less than 0.08% wt., or less than 0.05% wt. of hydrolyzed sulfoalkylating agent;
less than about 0.5, less than about 0.25, less than 0.2, less than about 0.15, less than about 0.1, and less than 0.05 Absorbance Units ("A.U.") of drug-degrading agent, as determined using a U.V. spectrophotometer and as measured at 245 nm to 270 nm by U.V. spectrophotometry for an aqueous solution containing about 500 mg SAE-CD per mL;
less than about 0.2, less than about 0.1, less than 0.05, less than about 0.01 A.U. of drug-degrading agent, as determined by a UV/visible spectrophotometer and as measured between 320 nm to 350 nm for an aqueous solution containing about 500 mg SAE-CD per mL.

The SAE-CD composition can be prepared by direct derivatization of an underivatized α-, β-, or γ-cyclodextrin or by further derivatization of a previously prepared cyclodextrin derivative. Such methods of derivatization include alterations in the known sequence of chemical synthetic steps for the preparation of water-soluble cyclodextrin derivatives. Suitable methods are described herein.

In some embodiments, the SAE-CD composition has an absorption of less than 0.2 A.U. due to a color-forming agent, as determined by UV/vis spectrophotometry at a wavelength of 320 nm to 350 nm for an aqueous solution containing 500 mg of the SAE-CD composition per mL of solution in a cell having a 1 cm path length.

In some embodiments, the SAE-CD composition further comprises one or more excipients.

The present invention is also directed to a process for preparing a SAE-CD composition comprising a sulfoalkyl ether cyclodextrin, the process comprising:
(a) mixing in an aqueous medium a cyclodextrin with a sulfoalkylating agent in the presence of an alkalizing agent to form an aqueous reaction milieu comprising a sulfoalkyl ether cyclodextrin, one or more unwanted components, and one or more drug-degrading impurities;
(b) conducting one or more separations to remove the one or more unwanted components from the aqueous milieu to form a partially purified aqueous solution comprising the sulfoalkyl ether cyclodextrin and the one or more drug-degrading impurities, wherein the one or more separations include a process selected from: ultrafiltration, diafiltration, centrifugation, extraction, solvent precipitation, and dialysis; and
(c) treating the partially purified aqueous solution with a phosphate-free activated carbon to provide the SAE-CD composition comprising the sulfoalkyl ether cyclodextrin and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

The present invention is also directed to a process for preparing a composition comprising an excipient and a SAE-CD composition, wherein the SAE-CD composition comprises a sulfoalkyl ether cyclodextrin, the process comprising:
(a) mixing in an aqueous medium a cyclodextrin with a sulfoalkylating agent in the presence of an alkalizing agent to form an aqueous reaction milieu comprising a sulfoalkyl ether cyclodextrin, one or more unwanted components, and one or more drug-degrading impurities;
(b) conducting one or more separations to remove the one or more unwanted components from the aqueous milieu to form a partially purified aqueous solution comprising the sulfoalkyl ether cyclodextrin and the one or more drug-degrading impurities, wherein the one or more separations include a process selected from: ultrafiltration, diafiltration, centrifugation, extraction, solvent precipitation, and dialysis;
(c) treating the partially purified aqueous solution with a phosphate-free activated carbon to provide the SAE-CD composition comprising the sulfoalkyl ether cyclodextrin and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length; and
(d) combining the SAE-CD composition with an excipient.

The present invention is also directed to a process for preparing a composition comprising one or more active agents and a SAE-CD composition, wherein the SAE-CD composition comprises a sulfoalkyl ether cyclodextrin, the process comprising:
(a) mixing in an aqueous medium a cyclodextrin with a sulfoalkylating agent in the presence of an alkalizing agent to form an aqueous reaction milieu comprising a sulfoalkyl ether cyclodextrin, one or more unwanted components, and one or more drug-degrading impurities;
(b) conducting one or more separations to remove the one or more unwanted components from the aqueous milieu to form a partially purified aqueous solution comprising the sulfoalkyl ether cyclodextrin and the one or more drug-degrading impurities, wherein the one or more separations include a process selected from: ultrafiltration, diafiltration, centrifugation, extraction, solvent precipitation, and dialysis;
(c) treating the partially purified aqueous solution with a phosphate-free activated carbon to provide the SAE-CD composition comprising the sulfoalkyl ether cyclodextrin and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length; and
(d) combining the SAE-CD composition with one or more active agents.

The present invention is also directed to a process comprising: mixing in an aqueous medium a cyclodextrin with sulfoalkylating agent in the presence of an alkalizing agent, thereby forming an aqueous reaction milieu comprising SAE-CD, one or more unwanted components, and one or more drug-degrading impurities; conducting one or more separations and/or purifications to remove the one or more unwanted components from the aqueous milieu thereby forming a partially purified aqueous solution comprising SAE-CD and one or more drug-degrading impurities; and repeatedly treating the partially purified aqueous solution with activated carbon, thereby eliminating or substantially reducing the amount of the one or more drug-degrading impurities therein and forming a aqueous composition comprising SAE-CD. The process can further comprise optionally degrading or removing excess sulfoalkylating agent, if any, present in the aqueous reaction milieu after formation of SAE-CD or after completion of the mixing. The process can further comprise optionally quenching the reaction.

The present invention is also directed to a product prepared by the above processes.

In some embodiments, the sulfoalkyl ether cyclodextrin in the processes of the present invention is a compound of Formula (1):

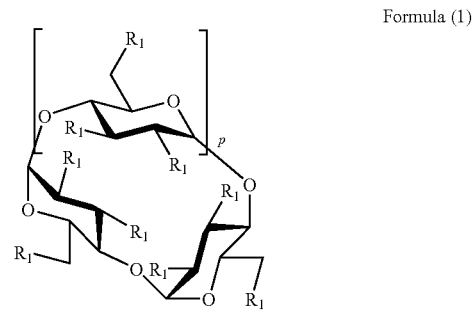

Formula (1)

wherein p is 4, 5 or 6, and $R_1$ is independently selected at each occurrence from —OH or -SAE-T; and wherein -SAE- is independently selected at each occurrence from a —O—($C_2$-$C_6$ alkylene)-$SO_3^-$ group, and -T is independently selected at each occurrence from pharmaceutically acceptable cations, provided that at least one $R_1$ is —OH and at least one $R_1$ is -SAE-T.

In some embodiments, -SAE- is a —O—($C_4$ alkylene)-$SO_3^-$ group at each occurrence, and -T is $Na^+$ at each occurrence.

In some embodiments, the treating comprises:

adding a phosphate-free particulate or powdered activated carbon to the partially purified aqueous solution while mixing, separating the activated carbon from the solution, and repeating the adding and the separating at least once until the amount of drug-degrading agent in the solution is reduced to a target level; or passing and recycling the partially purified aqueous solution through a mass of phosphate-free activated carbon in a flow-through apparatus until the amount of drug-degrading agent in the solution is reduced to a target level.

In some embodiments, the conducting comprises passing and recycling two or more times, wherein each passing is with a different mass of activated carbon.

In some embodiments, the activated carbon present during the conducting is about 12% by weight of the sulfoalkyl ether cyclodextrin, and the conducting is performed for at least about 2 hours.

In some embodiments, the mixing comprises: providing an aqueous alkaline composition comprising a cyclodextrin and adding to the composition a sulfoalkylating agent. In some embodiments, the mixing comprises providing a sulfoalkylating agent composition and adding to the composition an aqueous alkaline composition comprising a cyclodextrin.

The mixing can comprise: combining in an aqueous reaction medium an unsubstituted cyclodextrin starting material, and an alkyl sultone in an amount sufficient to effect a pre-determined degree of substitution, in the presence of a base to effect sulfoalkylation of the cyclodextrin; maintaining the pH of the reaction medium basic but at a level between about 9 and about 11 during the sulfoalkylation for a time sufficient to consume the cyclodextrin such that residual unreacted cyclodextrin reaches a level of less than 0.5% by weight based on the original weight of unsubstituted cyclodextrin starting material; adding base in an amount sufficient to effect completion of the sulfoalkylation; and adding, additional base following the completion, the base being added in an amount and under conditions sufficient to effect destruction of residual alkylsultone to a level less than 20 ppm or less than 2 ppm based on the weight of the solution.

In some embodiments, the mixing can comprise: combining in an aqueous reaction medium an unsubstituted cyclodextrin starting material with an alkyl sultone in an amount sufficient to effect a pre-determined degree of substitution, in the presence of an alkali metal hydroxide; conducting sulfoalkylation of the cyclodextrin at a pH of about 8 to about 11 until residual unreacted cyclodextrin is less than 0.5% by weight, or less than 0.1%; adding additional hydroxide in an amount sufficient to achieve the degree of substitution and allowing the sulfoalkylation to proceed to completion; and adding additional hydroxide following the completion, the hydroxide being added in an amount and under conditions sufficient to effect destruction of residual alkyl sultone to a level less than 20 ppm or less than 2 ppm based on the weight of the solution.

Degrading an excess sulfoalkylating agent can be required where unacceptable amounts of sulfoalkylating agent are present in the reaction milieu following termination of the mixing. Degrading can be conducted by: exposing the reaction milieu to an elevated temperature of at least 60° C., 60° C. to 85° C., or 60° C. to 80° C., for a period of at least 6 hours, or 6 hours to 72 hours, thereby degrading the sulfoalkylating agent in situ and reducing the amount of, or eliminating, the sulfoalkylating agent in the aqueous liquid.

Quenching can be conducted after a degrading is performed, or after a mixing but before a separating and/or one or more purifications. Quenching generally comprises: adding an acidifying agent to an alkaline SAE-CD containing solution to adjust the pH to about 5 to about 9, or about 6 to about 8, or about 6.5 to about 7.5.

In some embodiments, the process comprises conducting one or more separations to remove the one or more unwanted components from the aqueous milieu to form a partially purified aqueous solution comprising the sulfoalkyl ether cyclodextrin and the one or more drug-degrading impurities, wherein the one or more separations include a process selected from: ultrafiltration, diafiltration, centrifugation, extraction, solvent precipitation, and dialysis.

The separations can comprise: filtering the aqueous reaction milieu through a filtration medium to remove suspended solids and keep the filtrate; or centrifuging the aqueous reaction milieu and separating and keeping the supernatant; or extracting the suspended solids or impurities.

The purifications can comprise: dialyzing the reaction milieu or a liquid obtained therefrom. Dialyzing can be conducted by diafiltration, ultrafiltration and/or nanofiltration.

In some embodiments, the process comprises repeating one or more of the separations and/or purification. Repeatedly treating (i.e., treating more than once) can comprise: adding a granular or powdered activated carbon and/or other inert materials to the partially purified aqueous solution while mixing, separating the activated carbon from the solution, and repeating each adding and separating at least once or two or more times until the amount of drug-degrading agent(s) in the solution is reduced to at or below a target level; or passing and recycling the partially purified aqueous solution through a mass of activated carbon in a flow-through apparatus until the amount of drug-degrading agent(s) in the solution is reduced to at or below a target level. Repeatedly treating can concomitantly remove one or more other unwanted components, such as color-forming agent(s), protein, mineral, amino acid, metals, and carbon-adsorbable compound(s), in the partially purified solution.

The invention also provides a method of preparing a grade of SAE-CD by following these and other known methods of preparing SAE-CD with the exception that activated carbon not activated with phosphoric acid is used and multiple treatments with activated carbon are employed in the process. The activated carbon has a high surface area, meaning small particle size, and the process can be conducted in a batchwise or continuous format. The activated carbon can be powdered, granular, or encased within a flow-through apparatus.

The invention also provides a thermal method for reducing the amount of a sulfoalkylating agent in an aqueous liquid comprising a SAE-CD one or more other components, the method comprising exposing the aqueous liquid to elevated temperatures of at least 25° C., or 25° C. to 75° C., for at least 5 minutes, or 5 minutes to 200 minutes, thereby removing the sulfoalkylating agent in situ and reducing the amount of or eliminating the sulfoalkylating agent in the aqueous liquid.

In some embodiments, the invention provides a method of preparing a SAE-CD composition, the method comprising: exposing an initial cyclodextrin comprising at least one underivatized hydroxyl moiety, in aqueous alkaline media, to a substituent precursor for a period of time sufficient, at a temperature sufficient and at a solution pH sufficient to permit formation of a milieu comprising a cyclodextrin derivative composition having monomodal, bimodal, trimodal or multi-modal substitution profile, and optionally processing the milieu to remove undesired components thereby forming the SAE-CD composition. A cyclodextrin starting material for use with the present invention can include an underivatized cyclodextrin, a previously derivatized cyclodextrin, and combinations thereof.

In some embodiments, the invention provides a method of preparing a SAE-CD composition, the method comprising: providing a first liquid composition comprising substituent precursor; providing an alkaline second liquid composition comprising cyclodextrin (underivatized or derivatized); and adding the second liquid composition to the first liquid composition for a period of time sufficient, at a temperature sufficient and at a solution pH sufficient to permit formation of a milieu comprising a cyclodextrin derivative composition having a monomodal, bimodal, trimodal or multi-modal substitution profile, and optionally processing the milieu to remove undesired components thereby forming the combination composition. In some embodiments, the second liquid composition is added as a bolus, portionwise, dropwise, semi-continuously or continuously to the first liquid composition. In some embodiments, both the first and second liquid compositions are alkaline.

In some embodiments, the invention provides a method of preparing a SAE-CD composition, the method comprising: exposing a cyclodextrin starting material in neutral to alkaline aqueous media to substituent precursor at a temperature and for a period of time sufficient to provide an aqueous reaction milieu comprising SAE-CD, one or more unwanted components, and one or more drug-degrading components; degrading any unreacted substituent precursor, if any, in the milieu; subjecting the milieu to one or more separations and/or purifications to form a partially purified aqueous liquid comprising SAE-CD and one or more drug-degrading components; and treating the liquid with activated carbon at least two times to remove or reduce the amount of drug-degrading components present in the liquid, thereby forming an aqueous composition comprising SAE-CD.

The substituent precursor can be added incrementally or as a bolus, and the substituent precursor can be added before, during or after exposure of the cyclodextrin starting material to the optionally alkaline aqueous media. Additional alkaline material or buffering material can be added as needed to maintain the pH within a desired range. The derivatization reaction can be conducted at ambient to elevated temperatures. Once derivatization has proceeded to the desired extent, the reaction is optionally quenched by addition of an acid. The reaction milieu is further processed (e.g., solvent precipitation, filtration, centrifugation, evaporation, concentration, drying, chromatography, dialysis, and/or ultra-filtration) to remove undesired materials and form the target composition. After final processing, the composition can be in the form of a solid, liquid, semi-solid, gel, syrup, paste, powder, aggregate, granule, pellet, compressed material, reconstitutable solid, suspension, glass, crystalline mass, amorphous mass, particulate, bead, emulsion, or wet mass.

In some embodiments, the SAE-CD composition comprises a plurality of individual SAE-CD derivatives that differ in individual degree of substitution, such that the average degree of substitution for the SAE-CD composition is calculated, as described herein, from the individual degrees of substitution of the species. The individual cyclodextrin derivative species can have the same substituent(s), but differ in the number of substituent(s) per cyclodextrin molecule, or comprise different substituents that differ or are the same in number per cyclodextrin molecule.

The cyclodextrin of the SAE-CD derivative can comprise an α-, β-, or γ-cyclodextrin, or a combination thereof.

The regioisomerism of derivatization by the sulfoalkyl ether (SAE) substituent can also be varied as desired such that a majority of the substituents present can be preferentially located at a primary hydroxyl group or at one or both of the secondary hydroxyl groups of the cyclodextrin. In one embodiment, the primary distribution of substituents is C-3>C-2>C-6, while in other embodiments the primary distribution of substituents is C-2>C-3>C-6. The substitution pattern of the substituents can be determined by $^1$H-NMR or $^{13}$C-NMR, as described herein.

In some embodiments, a SAE-CD composition includes about 10% or less of each of an underivatized cyclodextrin. An underivatized cyclodextrin can be added to a composition, can be in the composition due to incomplete removal of a cyclodextrin starting material, and combinations thereof.

In some embodiments, a SAE-CD composition comprises a sulfoalkyl ether cyclodextrin comprising 50% or more, 50%, or less than 50% of the hydroxyl moieties being derivatized, in which all of the substituents of the sulfoalkyl ether cyclodextrin comprise similar alkylene (alkyl) radicals, or the substituents of the sulfoalkyl ether cyclodextrin comprise different alkylene (alkyl) radicals.

The SAE-CD composition of the invention can be used for substantially any known method or process wherein a cyclodextrin derivative provides utility. The composition can be used for the same process or method that its starting cyclodextrin derivative compositions are used. Suitable uses for a combination composition of the invention include use in pharmaceutical or non-pharmaceutical formulation. The combination composition of the invention can be used to solubilize, stabilize, taste-mask, suspend, immobilize, purify or extract one or more compounds formulated therewith. An active combination composition comprising a SAE-CD composition and one or more therapeutically effective agents can be used to treat (diagnose, prevent, cure, ameliorate, relieve, reduce the occurrence of, reduce the frequency of) a symptom, disease, or disorder that is therapeutically responsive to the one or more therapeutically effective agents.

In some embodiments, at least a portion of an active agent is complexed with a sulfoalkyl ether cyclodextrin.

The composition of the invention can be employed in compositions, formulations, methods and systems as such those disclosed in U.S. Pat. Nos. 5,134,127, 5,376,645, 6,046,177, 5,914,122, 5,874,418, 7,034,013, 6,869,939 and 6,133,248; U.S. Patent Pub. Nos. 2005/0164986, 2005/0186267, 2007/0175472, 2005/0250738, 2007/0020299, 2007/0202054, 2007/0020298, 2008/0194519, 2006/0258537, 2007/0020196; U.S. Appl. Nos. 60/914,555 and 60/952,771; and International Appl. Nos. PCT/US05/38933, PCT/US06/62346, PCT/US07/71758, PCT/US07/71748, PCT/US07/72442, PCT/US07/72387 and PCT/US07/78465, the entire disclosures of which are hereby incorporated by reference. The SAE-CD of the invention can also be used as a suitable substitute for other known grades of SAE-CD, particularly those known grades having lower purity, thereby resulting in compositions and formulations have greater stability, e.g., greater drug stability.

The invention includes combinations and sub-combinations of the various aspects and embodiments disclosed herein. These and other aspects of this invention will be apparent upon reference to the following detailed description, examples, claims, and attached drawings.

BRIEF DESCRIPTION OF THE DRAWINGS

The accompanying drawings, which are incorporated herein and form a part of the specification, illustrate one or more embodiments of the present invention and, together with the description, further serve to explain the principles of the invention and to enable a person skilled in the pertinent art to make and use the invention. The following drawings are given by way of illustration only, and thus are not intended to limit the scope of the present invention.

Figure 1:
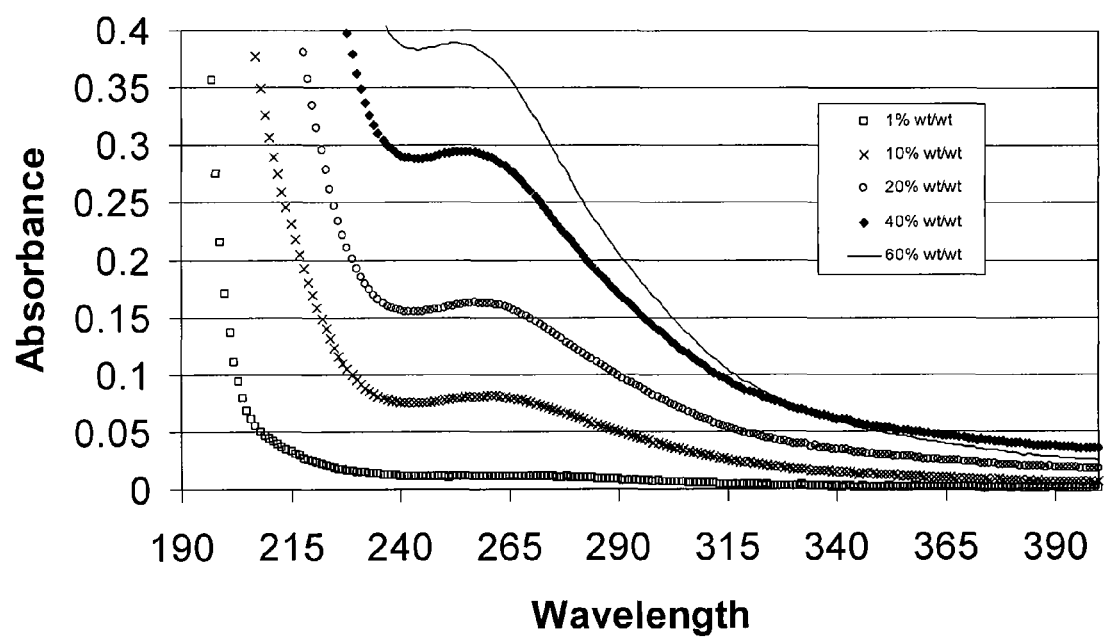
FIG. 1 provides a graphic representation of a UV/vis scan (190 nm to 400 nm) of solutions containing a SAE-CD composition after a single carbon treatment, in which the sulfoalkyl ether cyclodextrin concentration is varied from 1% to 60% by weight.

One or more embodiments of the present invention will now be described with reference to the accompanying drawings. In the drawings, like reference numbers can indicate identical or functionally similar elements. Additionally, the left-most digit(s) of a reference number can identify the drawing in which the reference number first appears.

DETAILED DESCRIPTION OF THE INVENTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

References to spatial descriptions (e.g., "above," "below," "up," "down," "top," "bottom," etc.) made herein are for purposes of description and illustration only, and should be interpreted as non-limiting upon the processes, equipment, compositions and products of any method of the present invention, which can be spatially arranged in any orientation or manner.

A SAE-CD composition of the invention provides unexpected advantages over other compositions containing structurally related cyclodextrin derivative compositions. By "structurally related" is meant, for example, that the substituent of the cyclodextrin derivative in the composition is essentially the same as the substituent of cyclodextrin derivative to which it is being compared. Exemplary advantages can include an improved ability of the combination composition to stabilize a neutral, cationic or anionic molecule, such as an active agent.

A "cyclodextrin derivative composition" is a composition having an average degree of substitution ("ADS") for a specified substituent. A cyclodextrin derivative composition comprises a distribution of cyclodextrin derivative species differing in the individual degree of substitution specified substituent for each species, wherein the specified substituent for each species is the same.

A composition of the invention can be a liquid, solid, suspension, colloid, pellet, bead, granule, film, powder, gel, cream, ointment, paste, stick, tablet, capsule, osmotic device, dispersion, emulsion, patch or any other type of formulation.

In some embodiments, a SAE-CD composition comprises a water-soluble cyclodextrin derivative of Formula 1:

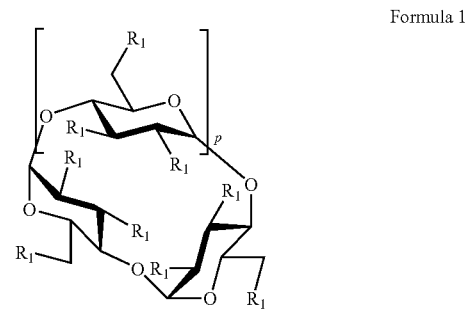

Formula 1 wherein: p is 4, 5 or 6;
$R_1$ is independently selected at each occurrence from —OH or -SAE-T;
-SAE- is a —O—($C_2$-$C_6$ alkylene)-$SO_3^-$ group, wherein at least one SAE is independently a —O—($C_2$-$C_6$ alkylene)-$SO_3^-$ group, a —O—$(CH_2)_g SO_3^-$ group, wherein g is 2 to 6, or 2 to 4, (e.g. —$OCH_2CH_2CH_2SO_3^-$ or —$OCH_2CH_2CH_2CH_2SO_3^-$); and -T is independently selected at each occurrence from the group consisting of pharmaceutically acceptable cations, which group includes, for example, $H^+$, alkali metals (e.g., $Li^+$, $Na^+$, $K^+$), alkaline earth metals (e.g., $Ca^{+2}$, $Mg^{+2}$), ammonium ions and amine cations such as the cations of ($C_1$-$C_6$)-alkylamines, piperidine, pyrazine, ($C_1$-$C_6$)-alkanolamine, ethylenediamine and ($C_4$-$C_8$)-cycloalkanolamine among others; provided that at least one $R_1$ is a hydroxyl moiety and at least one $R_1$ is -SAE-T.

When at least one $R_1$ of a derivatized cyclodextrin molecule is -SAE-T, the degree of substitution, in terms of the -SAE-T moiety, is understood to be at least one (1). When the term -SAE- is used to denote a sulfoalkyl-(alkylsulfonic acid)-ether moiety it being understood that the -SAE- moiety comprises a cation (-T) unless otherwise specified. Accordingly, the terms "SAE" and "-SAE-T" can, as appropriate, be used interchangeably herein.

Further exemplary SAE-CD derivatives include:

| $SAE_x$-α-CD | $SAE_x$-β-CD | $SAE_x$-γ-CD |
|---|---|---|
| $SEE_x$-α-CD | $SEE_x$-β-CD | $SEE_x$-γ-CD |
| $SPE_x$-α-CD | $SPE_x$-β-CD | $SPE_x$-γ-CD |
| $SBE_x$-α-CD | $SBE_x$-β-CD | $SBE_x$-γ-CD |
| $SPtE_x$-α-CD | $SPtE_x$-β-CD | $SPtE_x$-γ-CD |
| $SHE_x$-α-CD | $SHE_x$-β-CD | $SHE_x$-γ-CD | wherein SEE denotes sulfoethyl ether, SPE denotes sulfopropyl ether, SBE denotes sulfobutyl ether, SPtE denotes sulfopentyl ether, SHE denotes sulfohexyl ether, and x denotes the average degree of substitution. The salts thereof (with "T" as cation) are understood to be present.

The SAE-CD compositions comprise a cyclodextrin derivatized with anionic substituents that can be present in different salt forms. Suitable counterions include, but are not limited to, cationic organic atoms or molecules and cationic inorganic atoms or molecules. The SAE-CD compositions can include a single type of counterion or a mixture of different counterions. The properties of the SAE-CD compositions can be modified by changing the identity of the counterion present. For example, a first salt form of a sulfoalkyl ether cyclodextrin can provide a greater water activity reducing power than a different, second salt form of a sulfoalkyl ether cyclodextrin. Likewise, a sulfoalkyl ether cyclodextrin having a first degree of substitution can have a greater water activity reducing power than a second sulfoalkyl ether cyclodextrin having a different degree of substitution.

In some embodiments, a sulfoalkyl ether cyclodextrin possesses greater water solubility than a corresponding cyclodextrin from which a SAE-CD composition of the present invention is prepared. For example, in some embodiments, an underivatized cyclodextrin is utilized as a starting material, e.g., α-, β- or γ-cyclodextrin, commercially available from, e.g., WACKER BIOCHEM CORP. (Adrian, Mich.), and other sources. Underivatized cyclodextrins have limited water solubility compared to the SAE-CD compositions of the present invention. For example, underivatized α-CD, β-CD, γ-CD have a solubility in water solubility of about 145 g/L, 18.5 g/L, and 232 g/L, respectively, at saturation.

The water-soluble cyclodextrin derivative composition is optionally processed to remove a major portion (e.g., >50%) of an underivatized cyclodextrin, or other contaminants.

As used herein, a "substituent precursor" is used interchangeably with the term "sulfoalkylating agent" and refers to an agent or combination of agents and reaction conditions suitable for derivatizing a hydroxyl group of a cyclodextrin with a sulfoalkyl ether substituent. A substituent precursor can react with an oxygen atom of a hydroxyl group present on a cyclodextrin molecule to convert an —OH group to a sulfoalkyl ether group. Exemplary sulfoalkylating agents suitable for use with the present invention include, but are not limited to, an alkyl sultone (e.g., 1,4-butane sultone, 1,5-pentane sultone, 1,3-propane sultone, and the like).

The terms "alkylene" and "alkyl," as used herein (e.g., in the —O—($C_2$-$C_6$-alkylene)$SO_3^-$ group or in the alkylamine cations), include linear, cyclic, and branched, saturated and unsaturated (i.e., containing one or more double bonds), divalent alkylene groups and monovalent alkyl groups, respectively. The term "alkanol" in this text likewise includes both linear, cyclic and branched, saturated and unsaturated alkyl components of the alkanol groups, in which the hydroxyl groups can be situated at any position on the alkyl moiety. The term "cycloalkanol" includes unsubstituted or substituted (e.g., by methyl or ethyl)cyclic alcohols.

The cyclodextrin derivatives of the present invention can differ in their degree of substitution by functional groups, the number of carbons in the functional groups, molecular weight, the number of glucopyranose units present in the base cyclodextrin, and/or substitution pattern. In addition, the derivatization of a cyclodextrin with functional groups occurs in a controlled, although not exact manner. For this reason, the degree of substitution is actually a number representing the average number of functional groups per cyclodextrin (for example, $SBE_7$-β-CD, has an average of 7 substitutions per cyclodextrin). Thus, it has an average degree of substitution ("ADS") of about 7. In addition, the regiochemistry of substitution of the hydroxyl groups of the cyclodextrin is variable with regard to the substitution of specific hydroxyl groups of the hexose ring. For this reason, substitution of the different hydroxyl groups is likely to occur during manufacture of the derivatized cyclodextrin, and a particular derivatized cyclodextrin will possess a preferential, although not exclusive or specific, substitution pattern. Given the above, the molecular weight of a particular derivatized cyclodextrin composition can vary from batch to batch.

Within a given cyclodextrin derivative composition, the substituents of the cyclodextrin derivative(s) thereof can be the same. For example, SAE moieties can have the same type of alkylene (alkyl) radical upon each occurrence in a cyclodextrin derivative composition. In such an embodiment, the alkylene radical in the SAE moiety can be ethyl, propyl, butyl, pentyl or hexyl at each occurrence in a cyclodextrin derivative composition.

A cyclodextrin derivative composition comprises a distribution of a plurality of individual species, each species having an individual degree of substitution (IDS). The content of each of the cyclodextrin species in a particular composition can be quantified using capillary electrophoresis. The method of analysis (capillary electrophoresis, for example, for charged cyclodextrin derivatives) is sufficiently sensitive to distinguish between compositions having only 5% or more of individual cyclodextrin derivative species.

A cyclodextrin molecule can comprise 3v+6 hydroxyl groups that are available for derivatization, where v is typically about 4 to about 10. For v=4 (α-CD), "y" (the degree of substitution) can be 1 to 17. For v=5 (β-CD), "y" (the degree of substitution) can be 1 to 20. For v=6 (γ-CD), "y" (the degree of substitution) can be 1 to 23. In general, "y" can be an integer of 1 to 3v+g, 1 to 2v+g, or 1 to 1v+g, where "g" is an integer of 0 to 5.

The degree of substitution ("DS") refers to the number of sulfoalkyl ether substituents attached to a cyclodextrin molecule, in other words, the moles of substituent groups per mole of cyclodextrin. Therefore, each substituent has its own DS for an individual cyclodextrin derivative species. The average degree of substitution ("ADS") for a substituent is a measure of the total number of substituents present per cyclodextrin molecule for the distribution of cyclodextrin derivatives within a cyclodextrin derivative composition of the invention. Thus, $SAE_4$-CD has an ADS (per cyclodextrin molecule) of four (4).

A cyclodextrin derivative composition of the invention comprises a distribution of different individual cyclodextrin derivative species or molecules. More specifically, a SAE-CD derivative composition comprises plural SAE-CD species, each having a specific individual degree of substitution with regard to the SAE substituent. As a consequence, the ADS for SAE of a SAE-CD derivative composition represents an average of the individual DS (IDS) values of the population of individual molecules in the composition. For example, a $SAE_{5.2}$-CD composition comprises a distribution of plural $SAE_x$-CD molecules, wherein x (the DS for SAE groups) can vary from 1 to 10 or 1 to 11 for individual cyclodextrin molecules. However, the population of SAE-CD molecules is such that the average value for x (the ADS for SAE groups) is 5.2.

The Average Degree of Substitution ("ADS") for a cyclodextrin derivative composition can be calculated based upon the individual degree of substitution according to Formula (I):

$$ADS = \sum \left( \frac{(PAC)(MT)}{SCA} \times 100 \right) \bigg/ 100 \qquad (I)$$

wherein "PAC" refers to the Peak Area Count; "MT" refers to the Migration Time; and "SCA" refers to the Summation of Corrected Area. These values can be obtained using, e.g., capillary electrophoresis. The Corrected Area is the product of PAC×MT. The Individual Degree of Substitution ("IDS") is the Corrected Area divided by the Summation of Corrected Area [IDS=(PAC×MT)/SCA].

Variations among the individual cyclodextrin derivatives present in a SAE-CD composition can lead to changes in the complexation equilibrium constant, $K_{1:1}$, which in turn can affect the required molar ratio concentration of a SAE-CD composition to form a complex with, e.g., an active agent. The equilibrium constant can also be temperature-dependent and/or pH-dependent, and therefore allowances in the ratio of SAE-CD composition to active agent ratio are required such that an active agent remains solubilized during a temperature and/or pH fluctuation such as can occur during manufacture, storage, transport, use, and the like. The equilibrium constant can also vary due to the presence of other excipients (e.g., buffers, preservatives, antioxidants). Accordingly, the ratio of derivatized cyclodextrin to active agent can be varied from the ratios set forth herein in order to compensate for the above-mentioned variables.

The SAE-CD compositions used to form the combination composition can independently have a high to low ADS. The cyclodextrin derivative compositions can also have a wide or narrow "span," which refers to the number of individual species having a given degree of substitution within a SAE-CD composition. For example, a cyclodextrin derivative composition comprising a single species of cyclodextrin derivative having a single specified individual degree of substitution has a span of one, and in which case the individual degree of substitution of the cyclodextrin derivative equals the ADS of its cyclodextrin derivative composition. An electropherogram, for example, of a SAE-CD derivative with a span of one should have only one SAE-CD species with respect to degree of substitution. A cyclodextrin derivative composition having a span of two comprises two individual cyclodextrin derivative species differing in their individual degree of substitution, and its electropherogram, for example, would indicate two different cyclodextrin derivative species differing in degree of substitution. Likewise, the span of a cyclodextrin derivative composition having a span of three comprises three individual cyclodextrin derivative species differing in their individual degree of substitution. Since a combination composition of the invention comprises two or more different cyclodextrin derivative compositions, each having its own ADS, the span of the combination composition will be at least 4, meaning that each starting cyclodextrin derivative composition has a span of at least two.

In some embodiments, a cyclodextrin starting material includes a secondary hydroxyl group on the C-2 and C-3 positions of the glucopyranose residues forming the cyclodextrin and a primary hydroxyl on the C-6 position of the same. Each of these hydroxyl moieties is available for derivatization by substituent precursor. Depending upon the synthetic methodology employed, the substituent moieties can be distributed randomly or in a somewhat ordered manner among the available hydroxyl positions. Some embodiments of the invention includes a cyclodextrin derivative molecule wherein a minority of the substituent moieties is located at the C-6 position, and a majority of the substituent moieties is located at the C-2 and/or C-3 position. Still other embodiments of the invention includes a cyclodextrin derivative molecule wherein the substituent moieties are substantially evenly distributed among the C-2, C-3 and C-6 positions.

A combination composition of the invention can be prepared by: Method I, direct derivatization of an underivatized α-, β-, or γ-cyclodextrin); or Method II, further derivatization of a previously prepared cyclodextrin derivative The examples below detail several methods for preparing a SAE-CD composition. In general, an underivatized cyclodextrin starting material in neutral to alkaline aqueous media is exposed to substituent precursor. The substituent precursor can be added incrementally or as a bolus, and the substituent precursor can be added before, during or after exposure of the cyclodextrin starting material to the optionally alkaline aqueous media. Additional alkaline material or buffering material can be added as needed to maintain the pH within a desired range. The derivatization reaction can be conducted at ambient to elevated temperatures. Once derivatization has proceeded to the desired extent, the reaction is optionally quenched by addition of an acid. The reaction milieu is further processed (e.g., solvent precipitation, filtration, centrifugation, evaporation, concentration, drying, chromatography, dialysis, and/or ultrafiltration) to remove undesired materials and form the target composition. After final processing, the composition can be in the form of a solid, liquid, semi-solid, gel, syrup, paste, powder, aggregate, granule, pellet, compressed material, reconstitutable solid, suspension, glass, crystalline mass, amorphous mass, particulate, bead, emulsion, or wet mass.

The invention provides a process of making a SAE-CD composition comprising a sulfoalkyl ether cyclodextrin, optionally having a pre-determined degree of substitution, the process comprising: combining an unsubstituted cyclodextrin starting material with an alkyl sultone in an amount sufficient to effect the pre-determined degree of substitution, in the presence of an alkali metal hydroxide; conducting sulfoalkylation of the cyclodextrin within a pH of 9 to 11 until residual unreacted cyclodextrin is less than 0.5% by weight, or less than 0.1%; adding additional hydroxide in an amount sufficient to achieve the degree of substitution and allowing the sulfoalkylation to proceed to completion; and adding additional hydroxide to destroy any residual sultone.

Adding an additional hydroxide can be conducted using a quantity of hydroxide, and under conditions (i.e., amount of additional hydroxide added, temperature, length of time during which the sultone hydrolysis is conducted) such that the level of residual sultone in the aqueous crude product is reduced to less than 20 ppm or less than 2 ppm.

It is possible that the reaction milieu or the partially purified aqueous solution will comprise unreacted sulfoalkylating agent. The sulfoalkylating agent can be degraded in situ by adding additional alkalizing agent or by heating a solution containing the agent. Degrading an excess sulfoalkylating agent will be required where unacceptable amounts of sulfoalkylating agent are present in the reaction milieu following termination of the mixing. The sulfoalkylating agent can be degraded in situ by adding additional alkalizing agent or by heating a solution containing the agent.

Degrading can be conducted by: exposing the reaction milieu to an elevated temperature of at least 60° C., at least 65° C., or 60° C. to 85° C., 60° C. to 80° C. or 60° C. to 95° C. for a period of at least 6 hours, at least 8 hours, 8 hours to 12 hours, 6 hours to 72 hours, or 48 hours to 72 hours, thereby degrading the sulfoalkylating agent in situ and reducing the amount of or eliminating the sulfoalkylating agent in the aqueous liquid.

After the reaction has been conducted as described herein, the aqueous medium containing the sulfoalkyl ether cyclodextrin can be neutralized to a pH of about 7 in order to quench the reaction. The solution can then be diluted with water in order to lower viscosity, particularly if further purification is to be conducted. Further purifications can employed, including, but not limited to, diafiltration on an ultrafiltration unit to purge the solution of reaction by-products such as salts (e.g., NaCl if sodium hydroxide was employed as the base) and other low molecular weight by-products. The product can further be concentrated by ultrafiltration. The product solution can then be treated with activated carbon in order to improve its color, reduce bioburden, and substantially remove one or more drug degrading impurities. The product can be isolated by a suitable drying technique such as freeze drying, spray drying, or vacuum drum drying.

The reaction can be initially prepared by dissolving an unsubstituted α-, β-, or γ-cyclodextrin starting material in an aqueous solution of base, usually a hydroxide such as lithium, sodium, or potassium hydroxide. The base is present in a catalytic amount (i.e., a molar ratio of less than 1:1 relative to the cyclodextrin), to achieve a pre-determined or desired degree of substitution. That is, the base is present in an amount less than one molar equivalent for each hydroxyl sought to be derivatized in the cyclodextrin molecule. Because cyclodextrins become increasingly soluble in aqueous solution as the temperature is raised, the aqueous reaction mixture containing base and cyclodextrin should be raised to a temperature of about 50° C. to ensure complete dissolution. Agitation is generally employed throughout the course of the sulfoalkylation reaction.

After dissolution is complete, the alkyl sultone is added to start the sulfoalkylation reaction. The total amount of alkyl sultone added throughout the reaction will generally be in excess of the stoichiometric amount required to complete the reaction relative to the amount of cyclodextrin, since some of the alkylsultone is hydrolyzed and/or otherwise destroyed/degraded during the reaction such that it is not available for use in the sulfoalkylation reaction. The exact amount of alkylsultone to use for a desired degree of substitution can be determined through the use of trial runs. The entire amount of alkyl sultone needed to complete the reaction can be added prior to initiating the reaction. Because the system is aqueous, the reaction is generally conducted at a temperature between 50° C. and 100° C. The reaction can be conducted at a temperature less than 100° C., so that specialized pressure equipment is not required. In general, a temperature of 65° C. to 95° C. is suitable.

During the initial phase of the reaction (herein referred to as the pH-control phase), care should be taken to monitor the pH and maintain it at least basic, or in at a pH of about 8 to about 11. Monitoring of pH can be effected conventionally as by using a standard pH meter. Adjustment of the pH can be effected by adding an aqueous solution of hydroxide, e.g., a 10-15% solution. During the initial pH-control phase, unreacted cyclodextrin is reacted to the extent that less than 0.5% by weight, or less than 0.1% by weight, of unreacted cyclodextrin remains in solution. Substantially the entire initial charge of cyclodextrin is thus reacted by being partially substituted, but to less than the desired pre-determined degree of substitution. Residual cyclodextrin can be monitored throughout this initial phase, for example by HPLC as described below, until a desired endpoint of less than 0.5%, or less than 0.1%, of residual cyclodextrin starting material, has been achieved. The pH can be maintained and/or raised by adding concentrated hydroxide to the reaction medium continuously or in discrete amounts as small increments. Addition in small increments is particularly suitable.

Once a sulfoalkylation procedure has been standardized or optimized so that it is known that particular amounts of reactants can be combined in a procedure which produces the desired degree of substitution in conjunction with low residual cyclodextrin, then the procedure can simply be checked at the end, as opposed to throughout or during the initial pH-control, to ensure that a low level of residual (unreacted) cyclodextrin starting material has been achieved. The following table sets forth a relationship between the amount of butane sultone charged into a reactor and the resulting average degree of substitution of the SAE-CD.

| Butane Sultone Charged (Approximate equivalents of BS per mole of cyclodextrin) | Corresponding Approximate Predetermined ADS for SAE-CD formed |
| --- | --- |
| 2 | 2 |
| 3 | 3 |
| 4 | 4 |
| 5 | 5 |
| 6 | 5-5.5 |
| 7 | 5.5 to 6.5 |
| 8 | 6.5 to 7 |
| 9 | 7-8 |
| 12 | 8-9 |

It is noted that the initial pH of the reaction medium can be above 11, for example after combining the initial charge of cyclodextrin starting material and base, but prior to addition of alkyl sultone. After an alkyl sultone has been added and the reaction commences, however, the pH quickly drops, necessitating addition of base to maintain a basic pH of about 8 to about 11.

Once the level of residual unreacted cyclodextrin has reached a desired level, e.g., below 0.5% by weight, during the pH control stage, the pH can be raised to above 11, for example a level above 12, by adding additional base to drive the reaction to completion. The pH can be at least 12 so that the reaction proceeds at a reasonable rate, but not so high that unreacted alkyl sultone is hydrolyzed rapidly rather than reacting with cyclodextrin. During this latter phase of the reaction, additional substitution of the cyclodextrin molecule is effected until the pre-determined degree of substitution has been attained. The total amount of hydroxide added throughout the reaction is typically on the order of the amount stoichiometrically required plus a 10-20% molar excess relative to the amount of alkyl sultone employed. The addition of more than a 10-20% excess is also feasible. The reaction end point, as noted above, can be detected by HPLC. A suitable temperature is 65° C. to 95° C. The HPLC system typically employs an anion exchange analytical column with pulsed amperometric detection (PAD). Elution can be by gradient using a two-solvent system, e.g., Solvent A being 25 mM (millimolar) aqueous sodium hydroxide, and Solvent B being 1 M sodium nitrate in 250 mM sodium hydroxide.

Once the sulfoalkylation reaction is complete and the low residual cyclodextrin end point has been reached, additional hydroxide can be added to destroy and/or degrade any residual sultone. The additional hydroxide is typically added in an amount of 0.5 to 3 molar equivalents relative to cyclodextrin, and the reaction medium is allowed to continue heating at 65° C. to 95° C., typically for 6 hours to 72 hours.

After residual sultone destruction, the resulting crude product can be additionally treated to produce a final product by being diluted, diafiltered to reduce or rid the product of low molecular weight components such as salts, concentrated, carbon treated, and dried, usually to a level of less than 10% by weight of a cyclodextrin starting material corrected for water content.

The pH is initially monitored to ensure that it remains at about 8 to about 11 as the sulfoalkyl ether derivatization reaction proceeds. In this initial stage, addition of a hydroxide to facilitate the sulfoalkylation can be staged or step-wise.

Monitoring the pH of the reaction ensures that the reaction can be controlled such that the entire initial stock of cyclodextrin starting material is essentially reacted to the extent of effecting, on average, at least one sulfoalkyl substitution per cyclodextrin molecule. The entire cyclodextrin reactant is thus consumed at the beginning of the process, so that the level of residual (unreacted) cyclodextrin in the crude product is low, relative to the crude product produced by a process which features initially combining the entire stoichiometric or excess amount of base with cyclodextrin and alkyl sultone and allowing the reaction to proceed uncontrolled. After the entire charge of cyclodextrin starting material has been partially reacted, the remaining hydroxide can be added to drive the reaction to completion by finishing the sulfoalkyl substitution to the pre-determined, desired degree. After the initial charge of cyclodextrin has been consumed in the first pH-controlled phase, the rate of hydroxide addition is not critical. Thus, the hydroxide can be added (e.g., as a solution) continuously or in discrete stages. In addition, the pH of the reaction medium should be maintained above about 12 so that the rate of reaction is commercially useful.

Initial pH control provides a means for reducing certain by-products from the reaction mixture. For example, an acid is produced as a result of the sulfoalkylation and the pH of the reaction mixture tends to decrease (i.e., become more acidic) as the reaction proceeds. On one hand, the reaction is maintained basic because if the reaction medium becomes acidic, then the reaction will slow considerably or stop. Accordingly, the pH of the reaction medium should be maintained at a level of at least 8 by adding aqueous hydroxide as needed. On the other hand, if the pH is allowed to exceed a certain level, for example, a pH greater than 12, then the reaction can produce a high level of by-products such as 4-hydroxyalkylsulfonate and bis-sulfoalkyl ether, thus consuming the alkylsultone starting material. By monitoring the pH of the reaction solution and maintaining the pH at 8 to 12, or 8 to 11, the reaction proceeds while producing a relatively low-level of by-products, and a relatively clean reaction mixture containing relatively low levels of the aforementioned by-products is provided.

Reference above to a reactant being provided in an amount which is "stoichiometrically sufficient," and the like, is with respect to the amount of reactant needed to fully derivatize the cyclodextrin of interest to a desired degree of substitution. As used herein, an "alkali metal hydroxide" refers to LiOH, NaOH, KOH, and the like. If it is desired to produce a product suitable for parenteral administration, then NaOH can be used.

The degree of substitution can be controlled by using correspondingly lower or higher amounts of alkyl sultone, depending upon whether a lower or higher degree of substitution is desired. Generally, the degree of substitution that can be achieved is an average of from 4.5 to 7.5, 5.5 to 7.5, or 6 to 7.1.

The crude product of the process herein, i.e., the product obtained following residual alkylsultone destruction, contains a lower level of residual cyclodextrin than that produced by a process in which the base is initially added in a single charge, and is provided as a further feature of the invention. The crude product produced by the process of this invention typically contains less than 0.5% by weight residual cyclodextrin, or less than 0.1%. As explained below, the crude product is also advantageous in that it contains very low residual alkylsultone levels.

Typically, the crude aqueous cyclodextrin product solution obtained following residual alkylsultone destruction is purified by ultrafiltration, a process in which the crude product is contacted with a semipermeable membrane that passes low molecular weight impurities through the membrane. The molecular weight of the impurities passed through the membrane depends on the molecular weight cut-off for the membrane. For the instant invention, a membrane having a molecular weight cutoff of 1,000 Daltons ("Da") is typically employed. Diafiltrations and/or ultrafiltrations can be conducted with filtration membranes having a molecular weight cut-off of 500 Da to 2,000 Da, 500 Da to 1,500 Da, 750 Da to 1,250 Da, or 900 Da to 1,100 Da, or about 1,000 Da. The desired product which is in the retentate is then further treated with activated carbon to substantially remove drug-degrading impurities. The crude aqueous cyclodextrin product solution (i.e., obtained after residual alkyl sultone destruction but before purification) is advantageous in that it contains less than 2 ppm residual alkyl sultone based on the weight of the solution, less than 1 ppm, less than 250 ppb. The crude solution can also contain essentially no residual alkyl sultone.

A final, commercial product can be isolated at this point by, e.g., filtration to remove the activated carbon, followed by evaporation of the water (via, e.g., distillation, spray dying, lyophilization, and the like). The final product produced by the instant invention advantageously contains very low residual levels of alkyl sultone, e.g., less than 2 ppm based on the weight of the dry (i.e., containing less than 10% by weight water) final product, less than 1 ppm, less than 250 ppb, or essentially no residual alkyl sultone. The final product containing less than 250 ppb of alkyl sultone is accordingly provided as an additional feature of the invention. The alkyl sultone is reduced following completion of the sulfoalkylation to the desired degree of substitution by an alkaline hydrolysis treatment as previously described, i.e., by adding extra hydroxide solution in an amount and under conditions sufficient to reduce the amount of unreacted sultone in the dry product to the desired level below 2 ppm, less than 1 ppm, or less than 250 ppb.

Activated carbon suitable for use in the process of the present invention can be phosphate-free, and can be powder or granular, or a suspension or slurry produced therefrom. Generally, phosphate-free activated carbon is a carbon that was not activated using, or otherwise exposed to, phosphoric acid.

A wide variety of activated carbon is available. For example, Norit-Americas commercializes over 150 different grades and varieties of activated carbon under trademarks such as DARCO®, HYDRODARCO®, NORIT®, BENTONORIT®, PETRODARCO®, and SORBONORIT®. The carbons differ in particle size, application, method of activation, and utility. For example, some activated carbons are optimized for color and/or flavor removal. Other activated carbons are optimized for removal of protein, mineral, and/or amino acid moieties, or for clarifying solutions.

Activated carbons suitable for use according to the present invention include, but are not limited to: DARCO® 4×12, 12×20, or 20×40 granular from lignite, steam activated (Norit Americas, Inc., Amersfoort, Nebr.); DARCO® S 51 HF (from lignite, steam activated, powder); and SHIRASAGI® DC-32 powered or granular carbon from wood, zinc chloride activated (Takeda Chemical Industries, Ltd., Osaka, JP).

Carbon that is activated with phosphoric acid, as used in the prior art for purifying sulfoalkyl ether cyclodextrins, is generally unsuitable for use with the present invention, and includes: DARCO® KB-G, DARCO® KB-B and DARCO® KB-WJ, as well as NORIT® CASP and NORIT® CN1.

The loading ratio of activated carbon ultimately depends upon the amount or concentration of SAE-CD, color-forming agents, and drug-degrading agents in solution as well as the physical properties of the activated carbon used. In general, the weight ratio of a cyclodextrin to activated carbon is 5:1 to 10:1, 6:1 to 9:1, 7:1 to 9:1, 8:1 to 9:1, 8.3:1 to 8.5:1, 8.4:1 to 8.5:1, or 8.44:1 by weight per treatment cycle.

As used herein, "treatment cycle" refers to a contacting a predetermined amount of a cyclodextrin composition with a predetermined amount of activated carbon. A treatment cycle can be performed as a single treatment or as a multiple (recycling) pass-through treatment.

The Examples contained herein detail procedures used to evaluate and compare the efficiency of different grades, lots, sources, and types of activated carbon in removing the one or more drug-degrading components and one or more color-forming components present in an in-process milieu or solution of SAE-CD. In general, an in process milieu or solution is treated with activated carbon and agitation for 120 min. If a loose, particulate, or powdered form of activated carbon is used, it can be removed by filtration of a liquid containing the carbon through a filtration medium to provide the clarified solution.

The filtration membrane can include nylon, TEFLON®, PVDF or another compatible material. The pore size of the filtration membrane can be varied as needed according to the particle size or molecular weight of species being separated from the SAE-CD in a solution containing the same.

The Examples herein detail procedures for conducting one or more separations and/or purifications on an aqueous reaction milieu of the present invention. A reaction solution is diluted with aqueous solution and subjected to diafiltration during which the volume of the retentate is maintained substantially constant. The diafiltration can be conducted over a 1,000 Da filter such that one or more unwanted components pass through the filter but the majority of the sulfoalkyl ether present in the SAE-CD composition is retained in the retentate rather than passing through with the filtrate. The ultrafiltration is then conducted by allowing the volume of the retentate to decrease thereby concentrating the retentate. A filter having a molecular weight cut-off of about 1,000 Da can also be used for the ultrafiltration. The retentate comprises the SAE-CD, which can then be treated with activated carbon as described herein.

The one or more unwanted components can include, but are not limited to, low molecular weight impurities (i.e., impurities having a molecular weight of about 500 Da or less), water-soluble and/or water-insoluble ions (i.e., salts), hydrolyzed sulfoalkylating agent, 5-(hydroxymethyl)-2-furaldehyde, unreacted cyclodextrin starting material, degraded cyclodextrin species (e.g., degraded and/or ring-opened species formed from unreacted cyclodextrin, partially reacted cyclodextrin, and/or SAE-CD), unreacted sulfoalkylating agent (e.g., 1,4-butane sultone), and combinations thereof.

In some embodiments, the compositions of the present invention are substantially free of one or more drug degrading agents. The presence of one or more drug degrading agents can be determined, inter alia, by UV/visible ("UV/vis") spectrophotometry. As used herein, a "drug degrading agent" refers to a species, moiety, and the like, that degrades an active component in aqueous solution. In some embodiments, a drug-degrading species has an absorption in the UV/visible region of the spectrum, for example, an absorption maximum at a wavelength of 245 nm to 270 nm.

Not being bound by any particular theory, a drug-degrading agent, species, or moiety can include one or more low-molecular weight species (e.g., a species having a molecular weight less than 1,000 Da), such as, but not limited to a species generated as a side-product and/or decomposition product in the reaction mixture. As such, drug-degrading species include, but are not limited to, a glycosidic moiety, a ring-opened cyclodextrin species, a reducing sugar, a glucose degradation product (e.g., 3,4-dideoxyglucosone-3-ene, carbonyl-containing degradants such as 2-furaldehyde, 5-hydroxymethyl-2-furaldehyde and the like), and combinations thereof.

By "complexed" is meant "being part of a clathrate or inclusion complex with," i.e., a "complexed" therapeutic agent is part of a clathrate or inclusion complex with a sulfoalkyl ether cyclodextrin. The term "major portion" refers to 50% or greater, by weight, or on a molar basis. Thus, a formulation according to the present invention can contain an active agent of which more than about 50% by weight is complexed with a sulfoalkyl ether cyclodextrin. The actual percentage of active agent that is complexed will vary according to the complexation equilibrium binding constant characterizing the complexation of a specific cyclodextrin with a specific active agent. The invention also includes embodiments wherein the active agent is not complexed with the cyclodextrin or in which only a minor portion of the active agent is complexed with the sulfoalkyl ether cyclodextrin. It should be noted that a sulfoalkyl ether cyclodextrin, can form one or more ionic bonds with a positively charged compound. This ionic association can occur regardless of whether the positively charged compound is complexed with the cyclodextrin by inclusion complexation.

Among other uses, a SAE-CD composition of the present invention can be used to solubilize and/or stabilize a variety of different materials and to prepare formulations for particular applications. The present SAE-CD composition can provide enhanced solubility and/or enhanced chemical, thermochemical, hydrolytic and/or photochemical stability of other ingredients in a composition. For example, a SAE-CD composition can be used to stabilize an active agent in an aqueous medium. A SAE-CD composition can also be used to increase the solubility of an active agent in an aqueous medium.

The SAE-CD composition of the present invention includes one or more active agents. The one or more active agents included in the composition of the present invention can possess a wide range of water solubility, bioavailability and hydrophilicity. Active agents to which the present invention is particularly suitable include water insoluble, poorly water-soluble, slightly water-soluble, moderately water-soluble, water-soluble, very water-soluble, hydrophobic, and/or hydrophilic therapeutic agents. It will be understood by a person of ordinary skill in the art one or more active agents present in a composition of the present invention is independently selected at each occurrence from any known active agent and from those disclosed herein. It is not necessary that the one or more active agents form a complex with the sulfoalkyl ether cyclodextrin, or form an ionic association with the sulfoalkyl ether cyclodextrin.

Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents, pharmaceutically effective active agents, and other such compounds for pharmaceutical, veterinary, horticultural, household, food, culinary, agricultural, cosmetic, industrial, cleaning, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Representative pharmaceutically effective active agents include nutrients and nutritional agents, hematological agents, endocrine and metabolic agents, cardiovascular agents, renal and genitourinary agents, respiratory agents, central nervous system agents, gastrointestinal agents, antifungal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, corticosteroids, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes. Antifunal agents suitable for use with the SAE-CD composition of the present invention include, but are not limited to, posaconazole, voriconazole, clotrimazole, ketoconazole, oxiconazole, sertaconazole, tetconazole, fluconazole, itraconazole and miconazole. Antipsychotic agents suitable for use with the SAE-CD composition of the present invention include, but are not limited to, clozapine, prochlorperazine, haloperidol, thioridazine, thiothixene, risperidone, trifluoperazine hydrochloride, chlorpromazine, aripiprazole, loxapine, loxitane, olanzapine, quetiapine fumarate, risperidone and ziprasidone Exemplary cardiovascular agents include nootropic agents, antiarrhythmic agents, calcium channel blocking agents, vasodilators, antiadrenergics/sympatholytics, renin angiotensin system antagonists, antihypertensive agent combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, respiratory inhalant products, nasal decongestants, respiratory enzymes, lung surfactants, antihistamines, normarcotic antitussives, and expectorants. Exemplary central nervous system agents include CNS stimulants, narcotic agonist analgesics, narcotic agonist-antagonist analgesics, central analgesics, acetaminophen, salicylates, normarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, injectable local anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including H pylori agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, cephalosporins and related antibiotics, carbapenem, monobactams, chloramphenicol, quinolones, fluoroquinolones, tetracyclines, macrolides, spectinomycin, streptogramins, vancomycin, oxalodinones, lincosamides, oral and parenteral aminoglycosides, colistimethate sodium, polymyxin b sulfate, bacitracin, metronidazole, sulfonamides, nitrofurans, methenamines, folate antagonists, antifungal agents, antimalarial preparations, antituberculosis agents, amebicides, antiviral agents, antiretroviral agents, leprostatics, antiprotozoals, anthelmintics, and cdc anti-infective agents. Exemplary biologic and immunological agents including immune globulins, monoclonal antibody agents, antivenins, agents for active immunization, allergenic extracts, immunologic agents, and antirheumatic agents. Exemplary dermatological agents include topical antihistamine preparations, topical anti-infectives, anti-inflammatory agents, anti-psoriatic agents, antiseborrheic products, arnica, astringents, cleansers, capsaicin, destructive agents, drying agents, enzyme preparations, topical immunomodulators, keratolytic agents, liver derivative complex, topical local anesthetics, minoxidil, eflornithine hydrochloride, photochemotherapy agents, pigment agents, topical poison ivy products, topical pyrimidine antagonist, pyrithione zinc, retinoids, rexinoids, scabicides/pediculicides, wound healing agents, emollients, protectants, sunscreens, ointment and lotion bases, rubs and liniments, dressings and granules, and physiological irrigating solutions. Exemplary ophthalmic agents include agents for glaucoma, mast cell stabilizers, ophthalmic antiseptics, ophthalmic phototherapy agents, ocular lubricants, artificial tears, ophthalmic hyperosmolar preparations, and contact lens products. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, dna topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

The above-listed active agents should not be considered exhaustive and is merely exemplary of the many embodiments considered within the scope of the invention. Many other active agents can be administered with the formulation of the present invention.

A formulation of the invention can be used to deliver two or more different active agents. Particular combinations of active agents can be provided in a formulation of the invention. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; and 4) a first drug having a first type of biological activity and a different second drug having a different second type of biological activity. Exemplary combinations of active agents are described herein.

An active agent contained within a formulation of the invention can be present as its pharmaceutically acceptable salt. As used herein, "pharmaceutically acceptable salt" refers to derivatives of the disclosed compounds wherein the active agent is modified by reacting it with an acid and/or base as needed to form an ionically bound pair. Examples of pharmaceutically acceptable salts include conventional non-toxic salts or the quaternary ammonium salts of a compound formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Pharmaceutically acceptable salts suitable for use with the present invention can be prepared using an active agent that includes a basic or acidic group by conventional chemical methods. Suitable addition salts are found in *Remington's Pharmaceutical Sciences* (17th ed., Mack Publishing Co., Easton, Pa., 1985), the relevant disclosure of which is hereby incorporated by reference in its entirety.

The present invention is also directed to a method for stabilizing an active agent, the method comprising: providing a SAE-CD composition comprising a sulfoalkyl ether cyclodextrin and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length; and combining the SAE-CD composition with an active agent.

The method of stabilizing an active agent can be performed wherein the composition comprising one or more active agents and a SAE-CD composition comprising a sulfoalkyl ether cyclodextrin and less than 100 ppm of a phosphate is present as a dry solution, a wet solution, an inhalable composition, a parenteral composition, a solid solution, a solid mixture, a granulate, a gel, and other active agent compositions known to persons of ordinary skill in the art.

In some embodiments, the method of stabilizing an active agent provides about 2% or less, about 1.5% or less, about 1% or less, or about 0.5% or less of a drug-degradation impurity after the composition comprising one or more active agents and a SAE-CD composition comprising a sulfoalkyl ether cyclodextrin and less than 100 ppm of a phosphate is maintained at a temperature of about 80° C. for a period of about 120 minutes.

Similarly, in some embodiments, the method of stabilizing an active agent provides about an active agent assay of about 98% or more, about 98.5% or more, about 99% or more, or about 99.5% or more of the active agent after the composition comprising one or more active agents and a SAE-CD composition comprising a sulfoalkyl ether cyclodextrin and less than 100 ppm of a phosphate is maintained at a temperature of about 80° C. for a period of about 120 minutes.

Generally, the SAE-CD is present in an amount sufficient to stabilize the active agent. An amount sufficient can be a molar ratio of about 0.1:1 to about 10:1, about 0.5:1 to about 10:1, about 0.8:1 to about 10:1, or about 1:1 to about 5:1 (SAE-CD:active agent).

A cyclodextrin in the combination composition need not bind with another material, such as an active agent, present in a formulation containing it. However, if a cyclodextrin binds with another material, such a bond can be formed as a result of an inclusion complexation, an ion pair formation, a hydrogen bond, and/or a Van der Waals interaction.

An anionic derivatized cyclodextrin can complex or otherwise bind with an acid-ionizable agent. As used herein, the term acid-ionizable agent is taken to mean any compound that becomes or is ionized in the presence of an acid. An acid-ionizable agent comprises at least one acid-ionizable functional group that becomes ionized when exposed to acid or when placed in an acidic medium. Exemplary acid-ionizable functional groups include a primary amine, secondary amine, tertiary amine, quaternary amine, aromatic amine, unsaturated amine, primary thiol, secondary thiol, sulfonium, hydroxyl, enol and others known to those of ordinary skill in the chemical arts.

The degree to which an acid-ionizable agent is bound by non-covalent ionic binding versus inclusion complexation formation can be determined spectrometrically using methods such as $^{1}$H-NMR, $^{13}$C-NMR, or circular dichroism, for example, and by analysis of the phase solubility data for the acid-ionizable agent and anionic derivatized cyclodextrin. The artisan of ordinary skill in the art will be able to use these conventional methods to approximate the amount of each type of binding that is occurring in solution to determine whether or not binding between the species is occurring predominantly by non-covalent ionic binding or inclusion complex formation. Under conditions where non-covalent ionic bonding predominates over inclusion complex formation, the amount of inclusion complex formation, measured by NMR or circular dichroism, will be reduced even though the phase solubility data indicates significant binding between the species under those conditions; moreover, the intrinsic solubility of the acid-ionizable agent, as determined from the phase solubility data, will generally be higher than expected under those conditions.

As used herein, the term "non-covalent ionic bond" refers to a bond formed between an anionic species and a cationic species. A bond is non-covalent such that the two species together form a salt or ion pair. An anionic derivatized cyclodextrin provides the anionic species of the ion pair and the acid-ionizable agent provides the cationic species of the ion pair. Since an anionic derivatized cyclodextrin is multi-valent, a SAE-CD can form an ion pair with one or more acid-ionizable or otherwise cationic agents.

A liquid formulation of the invention can be converted to a solid formulation for reconstitution. A reconstitutable solid composition according to the invention comprises an active agent, a derivatized cyclodextrin and optionally at least one other pharmaceutical excipient. A reconstitutable composition can be reconstituted with an aqueous liquid to form a liquid formulation that is preserved. The composition can comprise an admixture (minimal to no presence of an inclusion complex) of a solid derivatized cyclodextrin and an active agent-containing solid and optionally at least one solid pharmaceutical excipient, such that a major portion of the active agent is not complexed with the derivatized cyclodextrin prior to reconstitution. Alternatively, the composition can comprise a solid mixture of a derivatized cyclodextrin and an active agent, wherein a major portion of the active agent is complexed with the derivatized cyclodextrin prior to reconstitution. A reconstitutable solid composition can also comprise a derivatized cyclodextrin and an active agent where substantially all or at least a major portion of the active agent is complexed with the derivatized cyclodextrin.

A reconstitutable solid composition can be prepared according to any of the following processes. A liquid formulation of the invention is first prepared, then a solid is formed by lyophilization (freeze-drying), spray-drying, spray freeze-drying, antisolvent precipitation, aseptic spray drying, various processes utilizing supercritical or near supercritical fluids, or other methods known to those of ordinary skill in the art to make a solid for reconstitution.

A liquid vehicle included in a formulation of the invention can comprise an aqueous liquid carrier (e.g., water), an aqueous alcohol, an aqueous organic solvent, a non-aqueous liquid carrier, and combinations thereof.

The formulation of the present invention can include one or more pharmaceutical excipients selected from the group consisting of a conventional preservative, antifoaming agent, antioxidant, buffering agent, acidifying agent, alkalizing agent, bulking agent, colorant, complexation-enhancing agent, cryoprotectant, electrolyte, glucose, emulsifying agent, oil, plasticizer, solubility-enhancing agent, stabilizer, tonicity modifier, flavors, sweeteners, adsorbents, antiadherent, binder, diluent, direct compression excipient, disintegrant, glidant, lubricant, opaquant, polishing agent, complexing agents, fragrances, other excipients known by those of ordinary skill in the art for use in formulations, and a combination thereof.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other α-hydroxy acids, hydrochloric acid, ascorbic acid, phosphoric acid, sulfuric acid, tartaric acid and nitric acid and others known to those of ordinary skill in the art.

As used herein, the term "antiadherent" is intended to mean an agent that prevents the sticking of solid dosage formulation ingredients to punches and dies in a tableting machine during production. Such compounds include, by way of example and without limitation, magnesium stearate, talc, calcium stearate, glyceryl behenate, polyethylene glycol, hydrogenated vegetable oil, mineral oil, stearic acid and other materials known to one of ordinary skill in the art.

As used herein, the term "binder" is intended to mean a substance used to cause adhesion of powder particles in solid dosage formulations. Such compounds include, by way of example and without limitation, acacia, alginic acid, carboxymethylcellulose sodium, poly(vinylpyrrolidone), a compressible sugar, ethylcellulose, gelatin, liquid glucose, methylcellulose, povidone and pregelatinized starch and other materials known to one of ordinary skill in the art.

When needed, binders can also be included in the dosage forms. Exemplary binders include acacia, tragacanth, gelatin, starch, cellulose materials such as methyl cellulose and sodium carboxymethylcellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in non-aqueous solvents, combinations thereof and others known to those of ordinary skill in the art. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, a conventional preservative is a compound used to at least reduce the rate at which bioburden increases, but maintains bioburden steady or reduces bioburden after contamination. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl or butyl parabens and others known to those of ordinary skill in the art. It is understood that some preservatives can interact with the cyclodextrin derivative thus reducing the preservative effectiveness. Nevertheless, by adjusting the choice of preservative and the concentrations of preservative and the cyclodextrin derivative adequately preserved formulations can be found.

As used herein, the term "diluent" or "filler" is intended to mean an inert substance used as a filler to create the desired bulk, flow properties, and compression characteristics in the preparation of a liquid or solid dosage form. Such compounds include, by way of example and without limitation, a liquid vehicle (e.g., water, alcohol, solvents, and the like), dibasic calcium phosphate, kaolin, lactose, dextrose, magnesium carbonate, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in compressed solid dosage forms. Such compounds include, by way of example and without limitation, dibasic calcium phosphate, and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid, EDTA, pentetate, and sodium metabisulfite and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, boric acid, sodium borate, citric acid, glycine, maleic acid, monobasic sodium phosphate, dibasic sodium phosphate, 4-(2-hydroxyethyl)-1-piperazineethanesulfonic acid, lactic acid, tartaric acid, potassium metaphosphate, potassium phosphate, monobasic sodium acetate, sodium bicarbonate, tris, sodium tartrate and sodium citrate anhydrous and dihydrate and others known to those of ordinary skill in the art.

A complexation-enhancing agent can be added to a formulation of the invention. When such an agent is present, the ratio of cyclodextrin/active agent can be changed. A complexation-enhancing agent is a compound, or compounds, that enhance(s) the complexation of the active agent with the cyclodextrin. Suitable complexation enhancing agents include one or more pharmacologically inert water-soluble polymers, hydroxy acids, and other organic compounds typically used in preserved formulations to enhance the complexation of a particular agent with cyclodextrins.

Hydrophilic polymers can be used as complexation-enhancing, solubility-enhancing and/or water activity reducing agents to improve the performance of formulations containing a CD-based preservative. Loftsson has disclosed a number of polymers suitable for combined use with a cyclodextrin (underivatized or derivatized) to enhance the performance and/or properties of the cyclodextrin. Suitable polymers are disclosed in *Pharmazie* 56:746 (2001); *Int. J. Pharm.* 212:29 (2001); Cyclodextrin: From Basic Research to Market, 10th Int'l Cyclodextrin Symposium, Ann Arbor, Mich., US, May 21-24, p. 10-15 (2000); PCT Int'l Pub. No. WO 99/42111; *Pharmazie* 53:733 (1998); *Pharm. Technol. Eur.* 9:26 (1997); *J. Pharm. Sci.* 85:1017 (1996); European Patent Appl. No. 0 579 435; Proc. of the 9th Int'l Symposium on Cyclodextrins, Santiago de Comostela, ES, May 31-Jun. 3, 1998, pp. 261-264 (1999); *S.T.P. Pharma Sciences* 9:237 (1999); *Amer. Chem. Soc. Symposium Series* 737 (Polysaccharide Applications):24-45 (1999); *Pharma. Res.* 15:1696 (1998); *Drug Dev. Ind. Pharm.* 24:365 (1998); *Int. J. Pharm.* 163:115 (1998); Book of Abstracts, 216th Amer. Chem. Soc. Nat'l Meeting, Boston, Aug. 23-27 CELL-016 (1998); *J. Controlled Release* 44:95 (1997); *Pharm. Res.* (1997) 14(11), 5203; *Invest. Opthalmol. Vis. Sci.* 37:1199 (1996); Proc. of the 23rd Int'l Symposium on Controlled Release of Bioactive Materials 453-454 (1996); *Drug Dev. Ind. Pharm.* 22:401 (1996); Proc. of the 8th Int'l Symposium on Cyclodextrins, Budapest, HU, Mar. 31-Apr. 2, 1996, pp. 373-376 (1996); *Pharma. Sci.* 2:277 (1996); *Eur. J. Pharm. Sci.* 4S:S144 (1996); 3rd Eur. Congress of Pharma. Sci. Edinburgh, Scotland, UK Sep. 15-17, 1996; *Pharmazie* 51:39 (1996); *Eur. J. Pharm. Sci.* 4S:S143 (1996); U.S. Pat. Nos. 5,472,954 and 5,324,718; *Int. J. Pharm.* 126:73 (1995); Abstracts of Papers of the Amer. Chem. Soc. 209:33-CELL (1995); *Eur. J. Pharm. Sci.* 2:297 (1994); *Pharm. Res.* 11:S225 (1994); *Int. J. Pharm.* 104:181 (1994); and *Int. J. Pharm.* 110:169 (1994), the entire disclosures of which are hereby incorporated by reference in their entirety.

Other suitable polymers are well-known excipients commonly used in the field of pharmaceutical formulations and are included in, for example, *Remington's Pharmaceutical Sciences*, 18th ed., pp. 291-294, A. R. Gennaro (editor), Mack Publishing Co., Easton, Pa. (1990); A. Martin et al., *Physical Pharmacy. Physical Chemical Principles in Pharmaceutical Sciences*, 3d ed., pp. 592-638 (Lea & Febinger, Philadelphia, Pa. (1983); A. T. Florence et al., *Physicochemical Principles of Pharmacy*, 2d ed., pp. 281-334, MacMillan Press, London, UK (1988), the disclosures of which are incorporated herein by reference in their entirety. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropylcellulose, their mixed ethers such as hydroxypropylmethylcellulose and other mixed ethers such as hydroxyethyl-ethylcellulose and hydroxypropylethylcellulose, hydroxypropylmethylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

As used herein, a fragrance is a relatively volatile substance or combination of substances that produces a detectable aroma, odor or scent. Exemplary fragrances include those generally accepted as safe by the U.S. Food and Drug Administration.

As used herein, the term "glidant" is intended to mean an agent used in solid dosage formulations to promote flowability of the solid mass. Such compounds include, by way of example and without limitation, colloidal silica, cornstarch, talc, calcium silicate, magnesium silicate, colloidal silicon, tribasic calcium phosphate, silicon hydrogel and other materials known to one of ordinary skill in the art.

As used herein, the term "lubricant" is intended to mean a substance used in solid dosage formulations to reduce friction during compression. Such compounds include, by way of example and without limitation, calcium stearate, magnesium stearate, polyethylene glycol, talc, mineral oil, stearic acid, and zinc stearate and other materials known to one of ordinary skill in the art.

As used herein, the term "opaquant" is intended to mean a compound used to render a coating opaque. An opaquant can be used alone or in combination with a colorant. Such compounds include, by way of example and without limitation, titanium dioxide, talc and other materials known to one of ordinary skill in the art.

As used herein, the term "polishing agent" is intended to mean a compound used to impart an attractive sheen to solid dosage forms. Such compounds include, by way of example and without limitation, carnauba wax, white wax and other materials known to one of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, bentonite, micro crystalline cellulose (e.g., AVICEL®), carboxymethylcellulose calcium, croscarmellose sodium, alginic acid, sodium alginate, cellulose polacrilin potassium (e.g., AMBERLITE®), alginates, sodium starch glycolate, gums, agar, guar, locust bean, karaya, pectin, tragacanth, crospovidone and other materials known to one of ordinary skill in the art.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. In one embodiment, the tonicity of the liquid formulation approximates the tonicity of blood or plasma.

As used herein, the term "antifoaming agent" is intended to mean a compound or compounds that prevents or reduces the amount of foaming that forms on the surface of the liquid formulation. Suitable antifoaming agents include dimethicone, simethicone, octoxynol and others known to those of ordinary skill in the art.

As used herein, the term "bulking agent" is intended to mean a compound used to add bulk to the solid product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

As used herein, the term "emulsifier" or "emulsifying agent" is intended to mean a compound added to one or more of the phase components of an emulsion for the purpose of stabilizing the droplets of the internal phase within the external phase. Such compounds include, by way of example and without limitation, lecithin, polyoxylethylene-polyoxypropylene ethers, polyoxylethylene-sorbitan monolaurate, polysorbates, sorbitan esters, stearyl alcohol, tyloxapol, tragacanth, xanthan gum, acacia, agar, alginic acid, sodium alginate, bentonite, carbomer, sodium carboxymethylcellulose, cholesterol, gelatin, hydroxyethyl cellulose, hydroxypropyl cellulose, octoxynol, oleyl alcohol, polyvinyl alcohol, povidone, propylene glycol monostearate, sodium lauryl sulfate, and others known to those of ordinary skill in the art.

A solubility-enhancing agent can be added to the formulation of the invention. A solubility-enhancing agent is a compound, or compounds, that enhance(s) the solubility of the active agent when in a liquid formulation. When such an agent is present, the ratio of cyclodextrin/active agent can be changed. Suitable solubility enhancing agents include one or more organic solvents, detergents, soaps, surfactant and other organic compounds typically used in parenteral formulations to enhance the solubility of a particular agent.

Suitable organic solvents include, for example, ethanol, glycerin, polyethylene glycols, propylene glycol, poloxomers, and others known to those of ordinary skill in the art.

Formulations comprising the SAE-CD composition of the invention can include oils (e.g., fixed oils, peanut oil, sesame oil, cottonseed oil, corn oil olive oil, and the like), fatty acids (e.g., oleic acid, stearic acid, isostearic acid, and the like), fatty acid esters (e.g., ethyl oleate, isopropyl myristate, and the like), fatty acid glycerides, acetylated fatty acid glycerides, and combinations thereof. Formulations comprising the SAE-CD composition of the invention can also include alcohols (e.g., ethanol, iso-propanol, hexadecyl alcohol, glycerol, propylene glycol, and the like), glycerol ketals (e.g., 2,2-dimethyl-1,3-dioxolane-4-methanol, and the like), ethers (e.g., poly(ethylene glycol) 450, and the like), petroleum hydrocarbons (e.g., mineral oil, petrolatum, and the like), water, surfactants, suspending agents, emulsifying agents, and combinations thereof.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

Formulations comprising the SAE-CD composition of the invention can also include biological salt(s), sodium chloride, potassium chloride, and other electrolyte(s).

Since some active agents are subject to oxidative degradation, a liquid formulation according to the invention can be substantially oxygen-free. For example, the headspace of a container containing a liquid formulation can made oxygen-free, substantially oxygen-free, or oxygen-reduced by purging the headspace with an inert gas (e.g., nitrogen, argon, carbon dioxide, and the like), or by bubbling an inert gas through a liquid formulation. For long-term storage, a liquid formulation containing an active agent subject to oxidative degradation can be stored in an oxygen-free or oxygen-reduced environment. Removal of oxygen from the formulation will enhance preservation of the formulation against aerobic microbes; whereas, addition of oxygen to the formulation will enhance preservation against anaerobic microbes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" or "subject" are taken to mean warm blooded animals such as mammals, for example, cats, dogs, mice, guinea pigs, horses, bovine cows, sheep, non-humans, and humans.

A formulation of the invention will comprise an active agent present in an effective amount. By the term "effective amount," is meant the amount or quantity of active agent that is sufficient to elicit the required or desired response, or in other words, the amount that is sufficient to elicit an appreciable biological response when administered to a subject.

The compositions of the present invention can be present in formulations for dosage forms such as a reconstitutable solid, tablet, capsule, pill, troche, patch, osmotic device, stick, suppository, implant, gum, effervescent composition, injectable liquid, ophthalmic or nasal solutions, or inhalable powders or solutions.

The invention also provides methods of preparing a liquid formulation comprising one or more active agents and a SAE-CD composition, wherein the SAE-CD composition comprises a sulfoalkyl ether cyclodextrin and less than 100 ppm of a phosphate. A first method comprises: forming a first aqueous solution comprising a SAE-CD composition; forming a second solution or suspension comprising one or more active agents; and mixing the first and second solutions to form a liquid formulation. A similar second method comprises adding one or more active agents directly to a first solution without formation of the second solution. A third method comprises adding a SAE-CD composition directly to the a solution/suspension containing one or more active agents. A fourth method comprises adding a solution comprising one or more active agents to a powdered or particulate SAE-CD composition. A fifth method comprises adding one or more active agents directly to a powdered or particulate SAE-CD composition, and adding the resulting mixture to a second solution. A sixth method comprises creating a liquid formulation by any of the above methods and then isolating a solid material by lyophilization, spray-drying, aseptic spray drying, spray-freeze-drying, antisolvent precipitation, a process utilizing a supercritical or near supercritical fluid, or another method known to those of ordinary skill in the art to make a powder for reconstitution.

Specific embodiments of the methods of preparing a liquid formulation include those wherein: 1) the method further comprises sterile filtering the formulation using a filtration medium having a pore size of 0.1 µm or larger; 2) the liquid formulation is sterilized by irradiation or autoclaving; 3) the method further comprises isolating a solid from the solution; 4) the solution is purged with nitrogen or argon or other inert pharmaceutically acceptable gas such that a substantial portion of the oxygen dissolved in, and/or in surface contact with, the solution is removed.

The invention also provides a reconstitutable solid pharmaceutical composition comprising one or more active agents, a SAE-CD composition and optionally at least one other pharmaceutical excipient. When this composition is reconstituted with an aqueous liquid to form a preserved liquid formulation, it can be administered by injection, infusion, topically, by inhalation or orally to a subject.

Some embodiments of the reconstitutable solid pharmaceutical composition includes those wherein: 1) the pharmaceutical composition comprises an admixture of a SAE-CD composition and a solid comprising one or more active agents and optionally at least one solid pharmaceutical excipient, such that a major portion of the active agent is not complexed with a sulfoalkyl ether cyclodextrin prior to reconstitution; and/or 2) the composition comprises a solid mixture of a SAE-CD composition and one or more active agents, wherein a major portion of the one or more active agents is complexed with the sulfoalkyl ether cyclodextrin prior to reconstitution.

A composition of the invention can be used in a pharmaceutical dosage form, pharmaceutical composition or other such combination of materials. These SAE-CD compositions are also useful as, but not limited to, analytical reagents, food and cosmetics adjuvants and/or additives, and as environmental clean-up agents.

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many embodiments contemplated by the present invention.

EXAMPLES

Example 1

Preparation of a $SBE_{2.0}$-β-CD Composition Having a Monomodal Distribution Profile A $SBE_2$-β-CD composition was prepared by the following procedure, in which an underivatized β-CD starting material present in an alkaline aqueous medium was derivatized with an SBE precursor to form a SBE-β-CD having an average degree of substitution of 2. The underivatized β-CD was dissolved in 6.5 equivalents of 3.6 N NaOH aqueous solution, heated to 50° C., and stirred until complete dissolution. The reaction temperature was then increased to 70° C. to 75° C. Two (2) equivalents of a sulfoalkylating agent (1,4-butanesultone) was then added over a period of 20 minutes. The total equivalents of sulfoalkylating agent added was proportional to the degree of substitution of the SAE-CD product. The pH was monitored for 4 hours and never dropped below 12. A second portion of 2.7 equivalents of 3.5 M NaOH was charged and the reaction was allowed to continue at 70° C. for at least an addition 16 hours. The reaction mixture was cooled and diluted with water (roughly one half the total reaction volume). The solution was neutralized with 7 M HCl to pH 6.5-7.5 and filtered through a 0.45 µm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with activated carbon (0.12 g activated carbon/gram of cyclodextrin), filtered through a 0.22 µm filter and neutralized (pH 6.5-7). The resulting solution was concentrated to roughly a 50% solution by rotary evaporation at 50° C. to 60° C. under less than 30 mmHg vacuum. The solution was freeze-dried to yield the $SBE_{2.0}$-β-CD as a white solid.

Example 2

Preparation of a $SBE_{3.1}$-β-CD Composition Having a Monomodal Distribution Profile A $SBE_{3.1}$-β-CD composition was prepared by the following procedure, in which an underivatized β-CD starting material present in an alkaline aqueous medium was derivatized with an SBE precursor to form a SBE-β-CD. The underivatized β-CD was dissolved in 6.5 equivalents of 3.6 N NaOH aqueous solution, heated to 50° C., and stirred until it was completely dissolved. The reaction temperature was then increased to 70° C. to 75° C. Three (3) equivalents of 1,4-butanesultone was added over a period of 15 minutes. The amount of equivalents added was proportional to the degree of substitution of the final product. The pH was monitored during the first 4 hours and never dropped below 12. A second portion of 2.7 equivalents of 3.5 M NaOH was charged and the reaction was allowed to continue at 70° C. for at least an addition 16 hours. The reaction mixture was cooled and diluted with water (roughly one-half the total reaction volume). The solution was neutralized with 7 M HCl to pH 6.5-7.5 and filtered through a 0.45 µm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 µm filter and neutralized (pH 6.5-7). The resulting solution was concentrated to roughly a 50% solution by Rotary evaporation at 50° C. to 60° C. under less than 30 mmHg vacuum. The solution was freeze-dried to yield a $SBE_{3.1}$-β-CD composition as a white solid.

Example 3

Preparation of a SBE$_{4.1}$-β-CD Composition Having a Monomodal Distribution Profile A SBE$_{4.1}$-β-CD composition was prepared by the following procedure, in which an underivatized β-CD starting material present in an alkaline aqueous medium was derivatized with an SBE precursor to form a SBE-β-CD. The underivatized β-CD was dissolved in 6.5 equivalents of 3.6 N NaOH aqueous solution, heated to 50° C., and stirred until complete dissolution. Once dissolution was complete the reaction temperature was increased to 70° C. to 75° C. Four (4) equivalents of 1,4-butanesultone was added over a period of 20 minutes. The amount of equivalents added was proportional to the degree of substitution of the final product. The pH was monitored during the first 4 hours and never dropped below 12. A second portion of 2.7 equivalents of 3.5 M NaOH was charged and the reaction was allowed to continue at 70° C. for at least an addition 16 hours. The reaction mixture was cooled and diluted with water (roughly one-half the total reaction volume). The solution was neutralized with 7 M HCl to pH 6.5-7.5 and filtered through a 0.45 μm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 μm filter and neutralized (pH 6.5-7.5). The resulting solution was concentrated to roughly a 50% solution by rotary evaporation at 50° C. to 60° C. under less than 30 mmHg vacuum. The solution was freeze-dried to yield a SBE$_{4.1}$-β-CD as a white solid.

Example 4

Preparation of a SBE$_{4.7}$-β-CD Composition Having a Monomodal Distribution Profile A SBE$_{4.7}$-β-CD composition was prepared by the following procedure, in which an underivatized β-CD starting material present in an alkaline aqueous medium was derivatized with an SBE precursor to form a SBE-β-CD. The underivatized β-CD was dissolved in 11 equivalents of 3.8 N NaOH aqueous solutions, heated and stirred until complete dissolution. Once dissolution was complete the reaction temperature was increased to 70° C. to 80° C. Six (6) equivalents of 1,4-butanesultone was added over a period of 20 minutes. The pH was monitored during the first 4 hours and never dropped below 13. The reaction was allowed to continue at 70° C. for at least an addition 16 hours. The reaction mixture was cooled and diluted with water (roughly one half the total reaction volume). The solution was neutralized with 8.4 M HCl to pH 6.5-7.5 and filtered through a 0.45 μm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was filtered through a 0.22 μm filter and neutralized (pH 6.5-7.5). The resulting solution was concentrated to roughly a 50% solution by Rotary evaporation at 50° C. to 60° C. under less than 30 mmHg vacuum. The solution was freeze-dried to yield a SBE$_{4.7}$-β-CD solid white solid.

Example 5

Preparation of a SBE$_{6.2}$-β-CD Composition Having a Monomodal Distribution Profile A SBE$_{6.2}$-β-CD composition was prepared by the following procedure, in which an underivatized β-CD starting material present in an alkaline aqueous medium was derivatized with an SBE precursor to form a SBE-β-CD. The underivatized β-CD was dissolved in 11 equivalents of 3.7 N NaOH aqueous solution, heated to 50° C., and stirred until complete dissolution. Once dissolution was complete the reaction temperature was increased to 70° C. to 75° C. Then, 6.8 equivalents of 1,4-butanesultone was added over a period of 35 minutes. The pH was monitored during the first 4 hours and never dropped below 12.9. The reaction was allowed to continue at 70° C. for at least an addition 16 hours. The reaction mixture was cooled and diluted with water (roughly one half the total reaction volume). The solution was neutralized with 7 M HCl to pH 6.5-7.5 and filtered through a 0.45 μm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with activated carbon (0.12 gram of activated carbon/gram of cyclodextrin), filtered through a 0.22 μm filter and neutralized (pH 6.5-7). The resulting solution was concentrated to roughly a 50% solution by Rotary evaporation at 50° C. to 60° C. under less than 30 mmHg vacuum. The solution was freeze-dried to yield a SBE$_{6.2}$-β-CD as a solid white solid.

Example 6

Preparation of a SBE$_{6.8}$-β-CD Composition Having a Monomodal Distribution Profile A SBE$_{6.8}$-β-CD composition was prepared by the following procedure, in which an underivatized β-CD starting material present in an alkaline aqueous medium was derivatized with an SBE precursor to form a SBE-β-CD. The underivatized β-CD was dissolved in 6.5 equivalents of 3.7 N NaOH aqueous solution, heated to 50° C., and stirred until complete dissolution. Once dissolution was complete the reaction temperature was increased to 70° C. to 75° C. Then, 8.7 equivalents of 1,4-butanesultone was added over a period of 40 minutes. The pH was monitored during the first 4 hours and never dropped below 8.6. A second portion of 4.4 equivalents of 3.9 M NaOH was charged and the reaction was allowed to continue at 70° C. for at least an addition 16 hours. The reaction mixture was cooled and diluted with water (roughly one half the total reaction volume). The solution was neutralized with 7 M HCl between 6.5 to 7.5 and filtered through a 0.45 μm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 μm filter and neutralized (pH 6.5-7). The resulting solution was concentrated to roughly a 50% solution by rotary evaporation at 50° C. to 60° C. under less than 30 mmHg vacuum. The solution was freeze-dried to provide $SBE_{6.8}$-β-CD as a white solid.

Example 7

Preparation of a $SBE_{4.2}$-γ-CD Composition Having a Monomodal Distribution Profile A $SBE_{4.2}$-γ-CD composition was prepared by the following procedure, in which an underivatized γ-CD starting material present in an alkaline aqueous medium was derivatized with an SBE precursor to form a SBE-γ-CD. The underivatized γ-CD was dissolved in 6.5 equivalents of 3.9 N NaOH aqueous solution, heated to 70° C., and stirred until complete dissolution. Once dissolution was complete the reaction temperature was increased to 70° C. to 75° C. Then, 4.2 equivalents of 1,4-butanesultone was added over a period of 110 minutes. The pH was monitored during the first 4 hours and never dropped below 12.6. A second portion of 4.2 equivalents of 6.3 M NaOH was charged and the reaction was allowed to continue at 70° C. for at least an addition 16 hours. The reaction mixture was cooled and diluted with water (roughly one third the total reaction volume). The solution was further treated with carbon (0.07 gram of carbon/gram of cyclodextrin), neutralized with 2.5 M HCl to pH 6-6.5 and filtered through a 0.45 μm filter. The solution was purified by Ultrafiltration using a 650 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was filtered through a 0.22 μm filter and neutralized (a pH 6-6.5). The resulting solution was concentrated to roughly a 50% solution by rotary evaporation at 50° C. to 60° C. under less than 30 mmHg vacuum. The solution was freeze-dried to yield a $SBE_{4.2}$-γ-CD as a white solid.

Example 8

Preparation of a $SBE_{4.8}$-γ-CD Composition Having a Monomodal Distribution Profile A $SBE_{4.8}$-γ-CD composition was prepared by the following procedure, in which an underivatized γ-CD starting material present in an alkaline aqueous medium was derivatized with an SBE precursor to form a SBE-γ-CD. The underivatized γ-CD was dissolved in 6.5 equivalents of 4 N NaOH aqueous solution, heated to 70° C., and stirred until complete dissolution. Once dissolution was complete the reaction temperature was increased to 70° C. to 75° C. Then, 4.5 equivalents of 1,4-butanesultone was added over a period of 103 minutes. The pH was monitored during the first 4 hours and never dropped below 12.4. A second portion of 4.3 equivalents of 6.3 M NaOH was charged and the reaction was allowed to continue at 70° C. for at least an addition 16 hours. The reaction mixture was cooled and diluted with water (roughly one third the total reaction volume). The solution was further treated with carbon (0.11 gram of carbon/gram of cyclodextrin), neutralized with 2.5 M HCl to pH 6-6.5 and filtered through a 0.45 μm filter. The solution was purified by Ultrafiltration using a 650 MWCO membrane. The Ultrafiltration end point was determined by capillary electrophoresis wherein the filtrate showed no or substantially no presence of 4-hydroxybutane-1-sulfonic acid and/or Disodium Bis (4-Sulfobutyl)Ether, and by Osmolarity, wherein the permeate samples had little to no ion present. The solution was filtered through a 0.22 μm filter and neutralized (pH 6-6.5). The resulting solution was concentrated to roughly a 50% solution by Rotary evaporation at 50° C. to 60° C. under less than 30 mmHg vacuum. The solution was freeze-dried to yield a $SBE_{4.8}$-γ-CD as a white solid.

Example 9

Preparation of a $SBE_{5.8}$-γ-CD Composition Having a Monomodal Distribution Profile A $SBE_{5.8}$-γ-CD composition was prepared by the following procedure, in which an underivatized γ-CD starting material present in an alkaline aqueous medium was derivatized with an SBE precursor to form a SBE-γ-CD. The γ-CD was dissolved in 6.5 equivalents of 4 N NaOH aqueous solution, heated to 70° C., and stirred until complete dissolution. Once dissolution was complete the reaction temperature was increased to 70° C. to 75° C. Then, 5.8 equivalents of 1,4-butanesultone was added over a period of 77 minutes. The pH was monitored during the first 4 hours and never dropped below 11.5. A second portion of 4 equivalents of 6.3 M NaOH was charged and the reaction was allowed to continue at 70° C. for at least an addition 16 hours. The reaction mixture was cooled and diluted with water (roughly one third the total reaction volume). The solution was neutralized with 2.5 M HCl to pH 7-7.25, treated with activated carbon (0.08 gram of activated carbon/gram of cyclodextrin), filtered through a 0.45 μm filter. The solution was purified by ultrafiltration using a 500 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by Osmolarity, wherein the permeate samples had little to no ion present. The solution was filtered through a 0.22 μm filter. The resulting solution was concentrated to roughly a 50% solution by Rotary evaporation at 50° C. to 60° C. under less than 30 mmHg vacuum. The solution was freeze-dried to yield a $SBE_{5.8}$-γ-CD as a white solid.

Example 10

Preparation of a $SBE_{6.1}$-γ-CD Composition Having a Monomodal Distribution Profile A $SBE_{6.1}$-γ-CD was prepared by the following procedure, in which an underivatized γ-CD starting material present in an alkaline aqueous medium was derivatized with an SBE precursor to form a SBE-γ-CD. The γ-CD was dissolved in 6.2 equivalents of 4 N NaOH aqueous solution at ambient temperature and stirred until complete dissolution. Then, 6.5 equivalents of 1,4-butanesultone was added. The pH was monitored during the first 4 hours and never dropped below 11. A second portion of 3.8 equivalents of 6.3 M NaOH was charged and the reaction was allowed to continue at 70° C. for at least an addition 16 hours. The solution was neutralized with 4.9 M HCl to pH 6-6.5, treated with activated carbon (0.08 gram of activated carbon/gram of cyclodextrin), filtered through a 0.45 μm filter. The solution was purified by ultrafiltration using a 500 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)eEther, and by osmolarity, wherein the permeate samples had little to no ion present. The solution was neutralized (pH 6-6.5) and filtered through a 0.22 μm filter. The resulting solution was concentrated to roughly a 50% solution by rotary evaporation at 50° C. to 60° C. under less than 30 mmHg vacuum. The solution was freeze-dried to yield a SBE$_{6.1}$-γ-CD as a white solid.

Example 11

Preparation of SBE-β-CD Having a Bimodal Distribution Profile and an AP-ADS of 4.6

An exemplary bimodal SBE-β-CD (AP-ADS 4.6) was made using the following, wherein the β-cyclodextrin was dissolved in 6.5 equivalents of 3.6 N NaOH. This solution was added over a period of 30 minutes to a stirred mixture of 6.5 equivalents of 1,4-butanesultone and 4.4 equivalents of 4.2 N NaOH at 70° C. to 75° C. The reaction was allowed to continue at 70° C. for at least an addition 16 hours. The reaction mixture was cooled and diluted with water (roughly one half the total reaction volume). The solution was neutralized with 7.3 M HCl to pH 6.5-7.5 and filtered through a 0.45 μm filter. The solution was purified by Ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 μm filter and neutralized (pH 6-7). The resulting solution was concentrated to roughly a 50% solution by rotary evaporation at 50° C. to 60° C. under less than 30 mmHg vacuum. The solution was freeze-dried to yield an AP-ADS 4.62 bimodal SBE-β-CD white solid.

Example 12

Preparation of SBE-β-CD Having a Bimodal Distribution Profile and an AP-ADS of 6.6

An exemplary bimodal SBE-β-CD (AP-ADS 6.6) was made using the following, in which a β-cyclodextrin was dissolved in 12.6 equivalents of 3.7 N NaOH. This solution was added over a period of 30 minutes to 6.5 equivalents of stirred 1,4-butanesultone at 70° C. to 75° C. The reaction was allowed to continue at 70° C. for at least an addition 16 hours. The reaction mixture was cooled and diluted with water (roughly one half the total reaction volume). The solution was neutralized with 7.3 M HCl to pH 6.5-7.5 and filtered through a 0.45 μm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 μm filter and neutralized (pH 6-7). The resulting solution was concentrated to roughly a 50% solution by Rotary evaporation at 50° C. to 60° C. under less than 30 mmHg vacuum. The solution was freeze-dried to yield a AP-ADS 6.6 bimodal SBE-β-CD white solid.

Example 13

Preparation of SBE-β-CD Having a Bimodal Distribution Profile and an AP-ADS of 6.9

An exemplary bimodal SBE-β-CD (AP-ADS 6.9) was made using the following, in which a β-cyclodextrin was dissolved in 10.9 equivalents of 3.8 N NaOH. This solution was added over a period of 65 minutes to 6.5 equivalents of stirred 1,4-butanesultone at 70° C. to 75° C. The reaction was allowed to continue at 70° C. for at least an addition 16 hours. The reaction mixture was cooled and treated with carbon (0.12 gram of carbon/gram of cyclodextrin). The solution was filtered, diluted with water (roughly one twentieth the total reaction volume). The solution was further neutralized with 8.25 M HCl to pH 6-7 and filtered through a 0.45 μm filter. The solution was purified by ultrafiltration using a 650 MWCO membrane. The ultrafiltration end point was determined by capillary electrophoresis wherein the filtrate showed no or substantially no presence of 4-Hydroxybutane-1-sulfonic acid and/or disodium bis(4-sulfobutyl)ether, and by osmolarity, wherein the permeate samples had little to no ion present. The resulting solution was concentrated to roughly a 50% solution by Rotary evaporation at 50° C. to 60° C. under less than 30 mmHg vacuum. The solution was freeze-dried to yield a AP-ADS 6.9 bimodal SBE-β-CD white solid.

Example 14

Preparation of SBE-γ-CD Having a Bimodal Distribution Profile and an AP-ADS of 3.8

An exemplary bimodal SBE-γ-CD (AP-ADS 3.8 was made using the following, in which a γ-cyclodextrin was dissolved in 12.5 equivalents of 3.7 N NaOH. This solution was added over a period of 30 minutes to 4.25 equivalents of stirred 1,4-butanesultone at 65° C. to 72° C. The reaction was allowed to continue at 70° C. for at least an addition 16 hours. The reaction mixture was cooled and neutralized with 8.9 M HCl to pH 6.5-7.5. The solution was diluted with water (roughly one half the total reaction volume). The resulting solution was filtered through a 0.45 μm filter. The solution was purified by Ultrafiltration using a 1000 MWCO membrane. The Ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 μm filter and neutralized (pH 6-7). The resulting solution was concentrated to roughly a 50% solution by Rotary evaporation at 50° C. to 60° C. under less than 30 mmHg vacuum. The solution was freeze-dried to yield a AP-ADS 3.8 bimodal SBE-γ-CD white solid.

Example 15

Preparation of SBE-γ-CD Having a Bimodal Distribution Profile and an AP-ADS of 6.5

An exemplary bimodal SBE-γ-CD (AP-ADS 6.5) was made using the following, in which a γ-cyclodextrin was dissolved in 12.5 equivalents of 3.7 N NaOH. This solution was added over a period of 35 minutes to 6.5 equivalents of stirred 1,4-butanesultone at 67° C. to 74° C. The reaction was allowed to continue at 70° C. for at least an addition 16 hours. The reaction mixture was cooled and neutralized with 8.5 M HCl to pH 6.5-7.5. The solution was diluted with water (roughly one half the total reaction volume). The resulting solution was filtered through a 0.45 μm filter. The solution was purified by Ultrafiltration using a 1000 MWCO membrane. The Ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 μm filter and neutralized (pH 6-7). The resulting solution was concentrated to roughly a 50% solution by Rotary evaporation at 50° C. to 60° C. under less than 30 mmHg vacuum. The solution was freeze-dried to yield a AP-ADS 6.5 bimodal SBE-γ-CD white solid.

Example 16

Preparation of SBE-γ-CD Having a Bimodal Distribution Profile and an AP-ADS of 6.9

An exemplary bimodal SBE-γ-CD (AP-ADS 6.9) was made using the following, in which a γ-cyclodextrin was dissolved in 12.5 equivalents of 3.7 N NaOH. This solution was added over a period of 38 minutes to 10 equivalents of stirred 1,4-butanesultone at 66° C. to 73° C. The reaction was allowed to continue at 70° C. for at least an addition 16 hours. The reaction mixture was cooled and neutralized with 8.5 M HCl to pH 6.5-7.5. The solution was diluted with water (roughly one half the total reaction volume). The resulting solution was filtered through a 0.45 μm filter. The solution was purified by ultrafiltration using a 1000 MWCO membrane. The ultrafiltration end point was determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution was further treated with carbon (0.12 gram of carbon/gram of cyclodextrin), filtered through a 0.22 μm filter and neutralized (pH 6-7). The resulting solution was concentrated to roughly a 50% solution by Rotary evaporation at 50° C. to 60° C. under less than 30 mmHg vacuum. The solution was freeze-dried to yield a AP-ADS 6.9 bimodal SBE-γ-CD white solid.

Example 17

Determination of Active Agent Solubility

Comparative evaluation of the solubilization effect of various sulfoalkyl ether cyclodextrin compositions on pharmaceutical active agents was determined as follows. A 0.04 M stock solutions of each selected cyclodextrin was prepared with purified water. Clarity of solutions was determined by visual inspection or instrumentally. A clear solution is at least clear by visual inspection with the unaided eye. Each pharmaceutical active agent, tested in duplicate, was combined with 2 mL or 4 mL of a SAE-CD aqueous solution.

Pharmaceutical active agents were weighed in amounts in excess of their anticipated solubility, and placed in TEFLON®-lined screw-capped vials. The active agents were present in amounts of at least 3 mg/mL. Each vial was then filled with the appropriate amount of cyclodextrin solution (either 2 mL or 4 mL). The vials were vortexed and sonicated to aid in wetting the solids with the fluid. The vials were then placed on a lab quake or a roller mixer for equilibration. The vials were visually inspected periodically to assure that the solids were adequately being wetted and in contact with the fluid. The fluid within the vials was then sampled periodically to determine the concentration of the pharmaceutical active agent present in solution. Samples were typically measured at 24 hr intervals.

Sampling of the vials to determine active agent solubility was performed by decanting 1 mL of solution from the vial followed by optional centrifuging. The removed supernatant was then filtered using a 0.22 μm syringe filter, and diluted with the mobile phase to an appropriate concentration within the standard curve. The samples were then analyzed by HPLC to determine concentration of the solubilized drug derivatives.

Example 18

Determination of Moisture Content

The following procedure was used to evaluate the moisture content the cyclodextrin derivatives. Determinations were performed in duplicate on 250 mg of each using a Brinkman Karl-Fischer Coulometer (Brinkman Instruments Co., IL). A known weight of solid cyclodextrin was added to the Karl-Fischer Coulometer and the total amount of water in the sample is measured. The total amount of water present is then converted to a percentage of the solid to give the percent moisture content of the sample.

Example 19

Analysis by Capillary Electrophoresis

The following procedure was used to analyze the SAE-CD derivative compositions by capillary electrophoresis. A Beckman P/ACE 2210 capillary electrophoresis system coupled with a UV absorbance detector (Beckman instruments, Inc., Fullereton, Calif.) was used to analyze solutions of SBE-β-CD and SBE-γ-CD derivatives. The separations were performed at 25° C. using a fused silica capillary (having a 50 μm inner diameter, a total length of 57 cm, and an effective length of 50 cm) with a pH adjusted running buffer of 30 mM benzoic acid and 100 mM TRIS (tris-hydroxymethyl-aminomethanol).

The capillary was treated with the following wash sequence before each injection with water, 0.01 N NaOH, and running buffer. The detector was set at 214 nm. The voltage was 30 kV. Samples were introduced by pressure injections: 20 seconds at 0.5 psi.

Example 20

An α-CD derivative composition having a monomodal distribution profile can be prepared according to any of Examples 1-10 or any of the literature methods cited herein, except that α-CD would be used in place of the β-CD or γ-CD. An exemplary SBE-α-CD is made using the following, wherein an α-cyclodextrin in an alkaline aqueous medium is derivatized with an SBE precursor to form the SBE-α-CD. The α-CD is dissolved in NaOH aqueous solution, heated to 70° C., and stirred until complete dissolution. Once dissolution is complete the reaction temperature is increased to 70° C. to 75° C. Then, 1,4-butanesultone was added over a period of at least 30 minutes. The pH is monitored during the first 4 hours and the reaction is allowed to continue at 70° C. for at least an addition 16 hours. The reaction mixture is cooled and diluted with water (roughly one third the total reaction volume). The solution is further treated with carbon (0.07 gram of carbon/gram of cyclodextrin), neutralized with HCl to pH 6-6.5 and filtered through a 0.45 μm filter. The solution is purified by ultrafiltration using a 650 MWCO membrane. The ultrafiltration end point is determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution is filtered through a 0.22 μm filter and neutralized (pH 6-6.5). The resulting solution is concentrated to roughly a 50% solution by rotary evaporation at 50° C. to 60° C. under less than 30 mmHg vacuum. The solution is freeze-dried to yield a SBE-α-CD white solid.

Example 21

Preparation of Combination Composition Having a Bimodal Distribution Profile

A previously prepared batch of cyclodextrin derivative composition, having a monomodal or bimodal distribution profile, is placed in aqueous alkaline liquid medium. A substituent precursor is placed in an optionally alkaline liquid medium in a vessel. The alkaline medium containing cyclodextrin derivative composition is added to the medium containing the substituent precursor in a drop-wise, portion-wise, semi-continuous, or continuous manner for a period of time sufficient, at a temperature sufficient, and a pH sufficient to form a reaction milieu comprising a combination composition having a bimodal or trimodal, respectively, distribution profile. For example, the dissolved batch of derivatized composition is added over a period of at least 30 minutes to the substituent precursor. The pH is monitored during the first 4 hours and the reaction is allowed to continue at 70° C. for at least an addition 16 hours. The reaction mixture is cooled and diluted with water (roughly one third the total reaction volume). The combination composition is optionally further purified to remove unwanted components and/or add wanted components. For example, the solution is further treated with carbon (0.07 gram of carbon/gram of cyclodextrin), neutralized with HCl to pH 6.5-7.5 and filtered through a 0.45 μm filter. The solution is purified by ultrafiltration using a 650 MWCO membrane. The ultrafiltration end point is determined by capillary electrophoresis wherein the filtrate showed no or substantially no presence of 4-hydroxybutane-1-sulfonic acid and/or disodium bis(4-sulfobutyl)ether, and by osmolarity, wherein the permeate samples had little to no ion present. The solution is filtered through a 0.22 μm filter and neutralized (pH 6-6.5). The resulting solution is concentrated to roughly a 50% solution by Rotary evaporation at 50° C. to 60° C. under less than 30 mmHg vacuum. The solution is freeze-dried to yield a SBE-α-CD white solid.

Example 22

$SBE_{6.6}$-β-CD Synthesis

A $SBE_{6.6}$-β-CD composition was synthesized according to the following procedure, in which a β-cyclodextrin in an alkaline aqueous medium was derivatized with an SBE precursor to form the $SBE_{6.6}$-β-CD. An aqueous solution of sodium hydroxide was prepared by charging 61.8 kg of sodium hydroxide to 433 kg of water for a 12.5% w/w solution. The reactor contents were heated to 40° C. to 50° C. before beginning the addition of 270 kg of β-CD over 30 to 60 minutes. The reaction temperature was adjusted to 65° C. to 95° C. before the addition of 259 kg of 1,4-butane sultone over 30 to 60 minutes. Over the next 6 hours the pH of the solution was maintained above 9 using an aqueous solution of sodium hydroxide. Following the reaction an additional 13.5 kg of sodium hydroxide as a 20% solution were charged to the reaction. The contents were maintained at 70° C. to 80° C. until the residual level of 1,4-butane sultone were sufficiently low. The contents were cooled to less than 30° C. and the reaction solution was adjusted to pH 6.5-7.5 with aqueous solution of hydrochloric acid. This process yielded 350 to 450 kg of SAE-CD.

Example 23

$SBE_{6.6}$-β-CD Diafiltration and Ultrafiltration

The $SBE_{6.6}$-β-CD of Example 22 was purified by the following procedure. The reaction solution was diluted with 800 kg of water. The solution was transferred and further diluted with 500 kg of water. Diafiltration was initiated using a Millipore Helicon Automated Ultrafiltration System using 1000 MWCO spiral wound regenerated cellulose membranes having at least 750 ft$^2$ of membrane area and maintaining a constant solution volume (±1%) until a sample of the returnate has 25 ppm or less of sodium chloride. The solution was concentrated by ultrafiltration until an appropriate solution mass was been achieved.

Example 24

$SBE_{6.6}$-β-CD Carbon Processing of the Present Invention

Following the diafiltration and ultrafiltration in Example 23, the $SBE_{6.6}$-β-CD was carbon purified by the following procedure. A column was charged with 32 kg (about 11-12% wt. (11.8-12% wt.) of the starting amount of β-cyclodextrin) of SHIRASAGI® DC32 granular activated carbon and washed thoroughly with water until the wash samples have a constant conductivity. The ratio of $SBE_{6.6}$-β-CD to activated carbon was about 8.4:1 to 8.5:1 (about 8.44:1). Once washed, the reaction solution was passed (recycled) through the carbon for at least 2 hours to complete a first treatment cycle.

A second column was charged with 32 kg (about 11-12% wt. of the starting amount of β-cyclodextrin) of SHIRASAGI® DC32 granular activated carbon and washed thoroughly with water until the wash samples have a constant conductivity. Once washed, the reaction solution was passed through the carbon for at least 2 hours to complete a second treatment cycle.

Example 25

$SBE_{6.6}$-β-CD Concentration and Isolation

The carbon-treated $SBE_{6.6}$-β-CD solutions prepared in Example 24 were concentrated and isolated using the following procedure: a $SBE_{6.6}$-β-CD solution was filtered through 0.65 μm and 0.22 μm filters and then concentrated at a reduced pressure of −0.6 bar to −0.7 bar at a temperature of 65° C. to 72° C., with agitation at 70 rpm to 100 rpm, until a solution having a $SBE_{6.6}$-β-CD concentration of 50% w/w was achieved. The concentrated solution was cooled to below 60° C., and then filtered through 0.65 μm and 0.22 μm filters. The filtered solution was then spray dried using a fluidized spray dryer ("FSD") system at an inlet temperature of 170° C., an initial pressure of 20 bar, and chambers 1-3 having set points of 125° C., 105° C., and 100° C., respectively.

Example 26

Determination of Cyclodextrin Substitution Pattern by $^1$H-NMR, $^{13}$C-NMR, COSY-NMR and HMQC on a Bruker AVANCE® 400 or 500 Instrument in $D_2O$ Solutions Determination of the substitution pattern is conducted according to the method of Example 6 of WO 2005/042584, the relevant disclosures of which are hereby incorporated by reference.

Example 27

$SBE_{6.6}$-β-CD Comparative Carbon Processing

An exemplary $SBE_{6.6}$-β-CD was carbon purified by the following procedure: a column was charged with 32 kg (about 11-12% wt. (11.8-12% wt.) of the starting amount of β-cyclodextrin in Example 22) of SHIRASAGI® DC32 granular activated carbon and washed thoroughly with water until the wash samples have a constant conductivity. Once washed the reaction solution was passed through the carbon for at least 2 hours.

Example 28

$SBE_{6.6}$-β-CD Impurity Analysis I $SBE_{6.6}$-β-CD samples treated either once or twice with activated carbon according to Examples 27 and 24, respectively, concentrated and isolated by the process described in Example 25, and were then analyzed by UV/vis spectrophotometry. The analysis was performed by dissolving an appropriate amount of $SBE_{6.6}$-β-CD in water (e.g., 0.1 g to 6 g of $SBE_{6.6}$-β-CD, corrected for water content, dissolved in 10 mL of water) to provide solutions containing from 1% to 60% w/w of the derivatized cyclodextrin.

Figure 2:
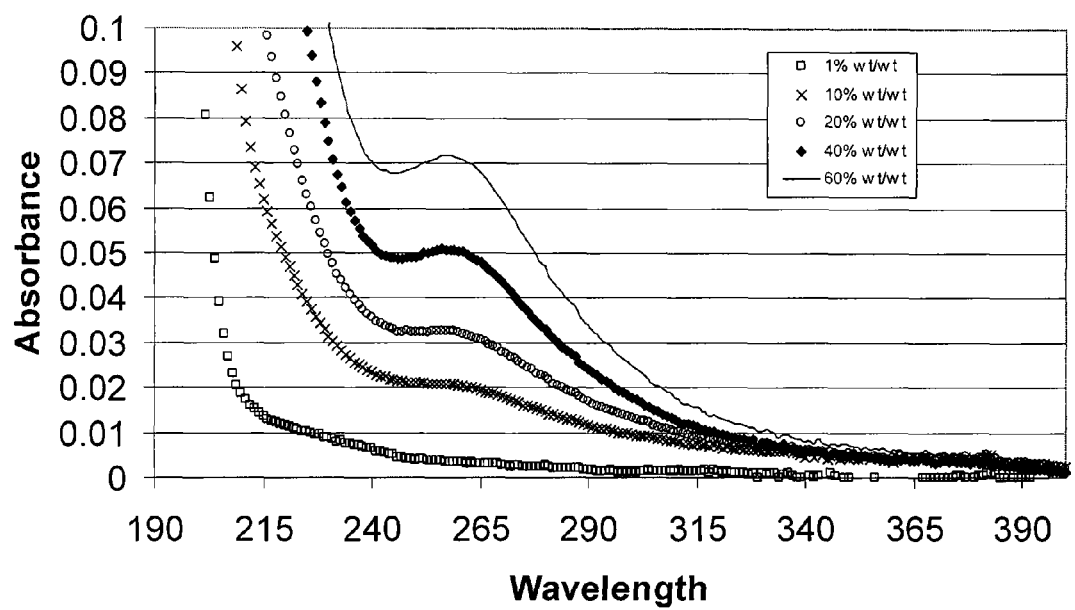
FIG. 2 provides a graphic representation of a UV/vis scan (190 nm to 400 nm) of solutions containing a SAE-CD composition after a second carbon treatment, in which the sulfoalkyl ether cyclodextrin concentration is varied from 1% to 60% by weight.

The carbon-treated cyclodextrin solutions were analyzed on a Perkin Elmer Lambda 35 UV/Vis spectrophotometer, scanning from 190 nm to 400 nm at a speed of 240 nm/min and a slit width of 1.0 nm. The samples were blanked against water before analysis. The UV/vis absorption spectra of various concentrations of $SBE_{6.6}$-β-CD solutions after one and two activated carbon treatments is provided graphically in FIGS. 1 and 2, respectively, which provide a graphic representation of the $SBE_{6.6}$-β-CD lots after one or two carbon treatments analyzed by the UV method. Referring to FIG. 1, the data shows that a higher concentration of impurities having an absorption in the UV/visible region of the spectrum is present when an $SBE_{6.6}$-β-CD solution is treated only once with activated carbon. Referring to FIG. 2, the data show that a second carbon treatment reduces the level of UV/vis absorbing impurities at least five fold or more.

Example 29

$SBE_{6.6}$-β-CD Impurity Analysis II

Colorimeter Analysis Method

The $SBE_{6.6}$-β-CD samples were analyzed by Hunter Labs Colorimeter using the following procedure: 50% w/w solutions were prepared by dissolving 15 grams of $SBE_{6.6}$-β-CD (corrected for water content) in 30 mL of water. The prepared solutions were analyzed on a Hunter Lab ULTRASCAN® colorimeter using Hunter Labs universal software, version 4.10. The instrument was standardized against USP matching color solutions, cupric sulfate CS, ferric chloride CS, and cobalt chloride CS. Samples were added to a 1 cm Hunter cuvette. The greater the DE value the more visible color a solution. Therefore $SBE_{6.6}$-β-CD Lot No. 17CX01.HQ00025 contained the most visible color while $SBE_{6.6}$-β-CD Lot No. 17CX01.HQ00029 contained the least visible color. $SBE_{6.6}$-β-CD Lot No. 17CX01.HQ00041 was slightly more than Lot No. 17CX01.HQ00029, but contained about five-fold fewer impurities having an absorption in the ultraviolet region of the spectrum. The table below includes the data obtained from analysis of SAE-CD lots with one or two carbon treatments analyzed by the Hunter colorimeter.

| Sample Description | L | a | DE |
| --- | --- | --- | --- |
| 50% w/w 17CX01.HQ00041 | 96.85 | −0.29 | 0.24 |
| 50% w/w 17CX01.HQ00029 | 96.88 | −0.32 | 0.16 |
| 50% w/w 17CX01.HQ00025 | 96.24 | −0.39 | 1.98 |

L = lightness; 100 for perfect white and 0 for black;
a = measures redness when positive, grey when zero, and greeness when negative;
b = measures yellowness when positive, grey when zero, and blueness when negative;
DE = Total Differences $\sqrt{(\Delta L^2 + \Delta a^2 + \Delta b^2)}$ from the Standard

Example 30

$SBE_{6.6}$-β-CD Impurity Analysis III

An exemplary $SBE_{6.6}$-β-CD sample was analyzed by analyzed by UV/Vis spectrophotometry using the following procedure: a 50% w/w $SBE_{6.6}$-β-CD solution was prepared by dissolving 54.1 grams of $SBE_{6.6}$-β-CD, corrected for water content, in a caustic solution of 12.5 grams of sodium hydroxide in 100 mL of water. The initial solution was analyzed on a PERKIN ELMER Lambda 35 UV/Vis spectrophotometer, scanning from 190 nm to 400 nm at a speed of 240 nm/min and a slit width of 1.0 nm. The sample was blanked against water before analysis. The solution was placed in a 60° C. oven for up to 168 hours. Solution samples were analyzed at 24 hours, 72 hours, 96 hours and 168 hours.

Figure 3:
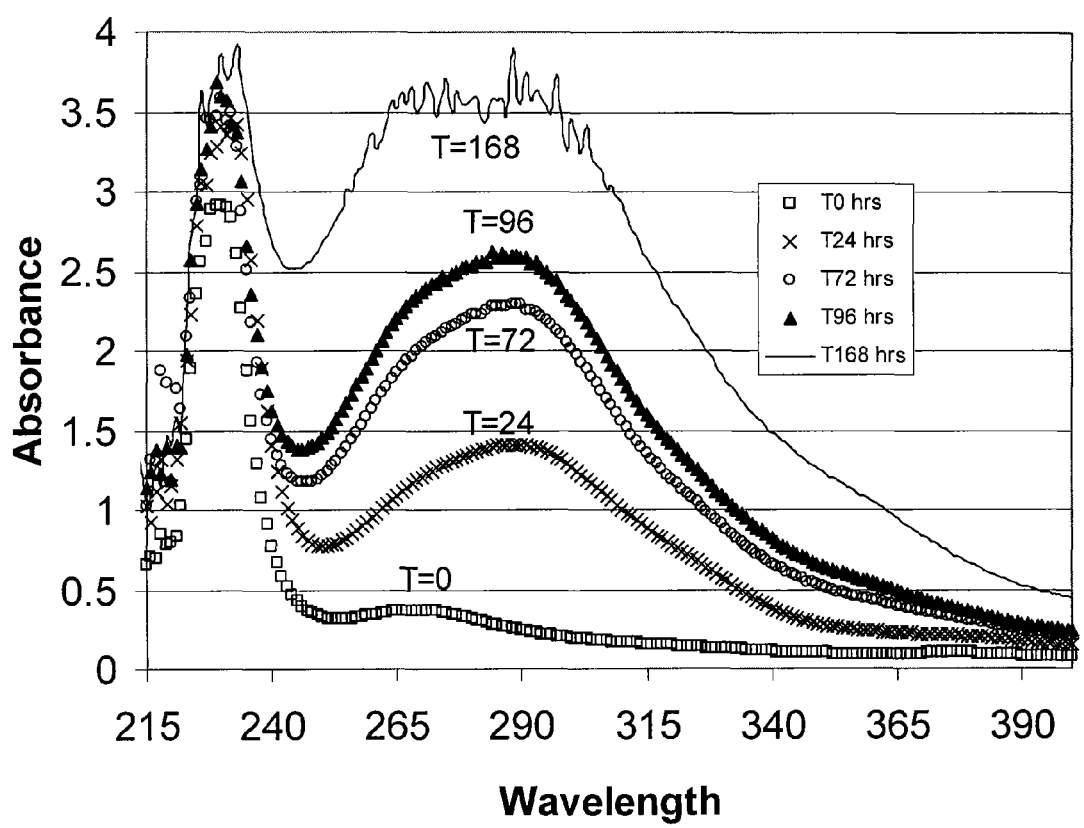
FIG. 3 provides a graphic representation of a UV/vis scan (190 nm to 400 nm) of a $SBE_{6.6}$-β-CD solution after thermal and caustic degradation at a temperature of 60° C. for a period of 0, 24, 72, 96 and 168 hours to demonstrate degradation of β-cyclodextrin and formation of drug-degrading impurities having an absorption at a wavelength of 245 nm to 270 nm and/or color-forming agents having an absorption at a wavelength of 320 nm to 350 nm.

FIG. 3 provides a graphical representation of the results from the thermal and caustic stress on the $SBE_{6.6}$-β-CD compositions. Referring to FIG. 3, the data shows that within 24 hours, a significant absorption at a wavelength of 245 nm to 270 nm has formed, and that this absorption increases with the duration of thermal and caustic exposure. By 168 hours (7 days), the absorption maximum at a wavelength of 245 nm to 270 nm has increased to an equal magnitude with the absorption having a maximum at about 230 nm. Also of note is that the absorption at a wavelength of 320 nm to 350 nm also increases with time of exposure. The data shows that a drug-degrading impurity having an absorption at a wavelength of 245 nm to 270 nm, as well as a color forming agent having an absorption at a wavelength of 320 nm to 350 nm, increase in concentration over time under exposure to heat and/or caustic conditions.

Example 31

$SBE_{6.6}$-β-CD Formulation Stability

Comparative evaluation of the stability of various lots of $SBE_{6.6}$-β-CD that underwent a single or a double treatment with activated carbon (according to Examples 27 and 24, respectively) were formulated with a glucocorticosteroid (budesonide) and an excipient (water), and were examined by HPLC. The general procedure is provided below.

$SBE_{6.6}$-β-CD solutions (7.5% w/w, formulated with $SBE_{6.6}$-β-CD Lot Nos. 17CX01.HQ00025, 17CX01.HQ00029 and 17CX01.HQ00041), were prepared by dissolving about 7.5 grams of $SBE_{6.6}$-β-CD (corrected for water content) in 100 mL of water. A glucocorticosteroid was weighed in amounts in excess of the anticipated solubilities directly into TEFLON®-lined screw-capped containers. Approximately 275 μg/mL of the glucocorticoid steroid was vigorously stirred for 2 hours in an amber glass container. At the end of the agitation time, the glucocorticosteroid solution was filtered using a 0.22 μm syringe filter.

Control solution samples were removed before autoclaving. Aliquots of the solutions were autoclaved for four 20 minute cycles at 121° C. The samples were then analyzed by HPLC to determine assay content and the level of impurities formed during the heating cycles. Solution samples of $SBE_{6.6}$-β-CD were prepared and analyzed on a PERKIN ELMER Lambda 35 UV/Vis spectrophotometer, scanning from 190 nm to 400 nm at a speed of 240 nm/min and a slit width of 1.0 nm to determine the UV content.

Glucocorticoid Steroid HPLC Conditions:

| | |
|---|---|
| Instrument: | Shimadzu PROMINENCE ® |
| Column: | GL Science INERTSIL ® S-3 (4.6 mm × 250 mm × 5 μm) |
| Mobile Phase A: | 64% phosphate buffer/33.5% acetonitrile/ 2.5% methanol |
| Mobile Phase B: | 47.5% phosphate buffer/50% acetonitrile/ 2.5% methanol |
| Wavelength: | 240 nm |
| Flow Rate: | 1.5 mL/min |
| Column Temp: | 40° C. |
| Injection Volume: | 50 μL |

$SBE_{6.6}$-β-CD Solution UV Analysis

| $SBE_{6.6}$-β-CD Lot No. | UV Analysis (Max Abs @ λ = 245-270 nm) |
|---|---|
| 50% w/w 17CX01.HQ00041 | 0.130 |
| 50% w/w 17CX01.HQ00029 | 0.339 |
| 50% w/w 17CX01.HQ00025 | 0.652 |

Assay and Impurity Analysis of Heat-Stressed $SBE_{6.6}$-β-CD/ Glucocorticosteroid The results of the study show that $SBE_{6.6}$-β-CD compositions that contain a low amount of UV-active drug-degrading impurities provide more stable API formulations and lower API degradation. The addition of a higher $SBE_{6.6}$-β-CD solution color does not dictate a higher level of glucocorticosteroid impurities. Furthermore, based on the stability of the glucocorticosteroid, $SBE_{6.6}$-β-CD Lot No. 17CX01.HQ00041 was significantly better at stabilizing the isomers of the glucocorticosteroid than $SBE_{6.6}$-β-CD Lot No. 17CX01.HQ00025.

Example 32

$SBE_{6.6}$-β-CD Formulation Stability with Triazole Antifungal API $SBE_{6.6}$-β-CD compositions that underwent single- or double-treatment with activated carbon (according to Examples 27 and 24, respectively) were formulated with a triazole antifungal API (posaconazole, which was purchased from Schering-Plough as an aqueous oral suspension, NOXAFIL®) and the stability of the API formulation was determined by Hunter colorimetric and HPLC analysis. The formulation procedure is provided below.

Aqueous solution samples of a triazole antifungal API (5 mg/mL) and a $SBE_{6.6}$-β-CD composition (100 mM, pH 3) were prepared using $SBE_{6.6}$-β-CD Lot Nos. 17CX01.HQ00044, 17CX01.HQ00037, 17CX01.HQ00035, 17CX01.HQ00033 and 17CX01.HQ00029. All solution samples were filtered through 0.22 μm PVDF filter, and separated into vials. The UV/Vis absorption of a portion of the initial solutions was measured using a 1 cm Hunter cuvette on a PERKIN ELMER Lambda 35 UV/Vis spectrophotometer, scanning from 190 nm to 400 nm at a speed of 240 nm/min and a slit width of 1.0 nm, and analyzed on a Hunter Labs ULTRASCAN® colorimeter using Hunter Labs universal software, version 4.10. The samples were blanked against water before measurement. The remaining portions of samples were then placed into a 60° C. oven for 7 days and then reanalyzed for color changes using the same procedure. The data is shown in the following tables.

| | Impurities | | Assay | | | |
|---|---|---|---|---|---|---|
| Lot No. | A Area % | B[1] Area % | R-GS[1] Area % | S-GS[3] Area % | GS Total Area % | Δ % |
| Glucocorticosteroid ("GS") Std. | 0.001 | 0.127 | 51.888 | 47.497 | 99.385 | 0 |
| 17CX01.HQ00025[a],* | 0.010 | 0.132 | 51.799 | 47.483 | 99.282 | 0.103 |
| 17CX01.HQ00025[b] | 0.096 | 0.134 | 32.879 | 36.213 | 69.092 | 30.293 |
| 17CX01.HQ00029[a],* | 0.003 | 0.140 | 51.784 | 47.498 | 99.282 | 0.103 |
| 17CX01.HQ00029[b] | 0.207 | 0.164 | 50.656 | 46.86 | 97.516 | 1.869 |
| 17CX01.HQ00041[a],* | 0.001 | 0.130 | 51.778 | 47.526 | 99.304 | 0.081 |
| 17CX01.HQ00041[b] | 0.058 | 0.139 | 38.138 | 39.791 | 77.929 | 21.456 |

[1]Impurity B was identified as the S-11-keto-derivative of the glucocorticosteroid.
2 "R-GS" refers to the R-enantiomer of the glucocorticosteroid.
[3]"S-GS" refers to the S-enantiomer of the glucocorticosteroid.
*Lot Nos. 17CX01.HQ00025 and 17CX01.HQ00041 underwent a single treatment with activated carbon (see Example 27), while Lot No. 17CX01.HQ00029 underwent a double activated carbon treatment (see Example 24).
[a]As measured initially (t = 0).
[b]Treatment for 80 minutes at 121° C.

SBE$_{6.6}$-β-CD Initial Solutions: UV/Vis Analysis

| 30% SBE$_{6.6}$-β-CD Solutions Lot No. | Carbon Processing Condition | UV analysis (Max Abs @ λ = 245-270 nm) |
|---|---|---|
| 17CX01.HQ00044 | 2 Granular carbon treatments (SHIRASAGI ® DC-32) | 0.05 |
| 17CX01.HQ00037 | 2 Granular carbon treatments (SHIRASAGI ® DC-32) | 0.11 |
| 17CX01.HQ00035 | 2 Granular carbon treatments (SHIRASAGI ® DC-32) | 0.16 |
| 17CX01.HQ00033 | 1 Granular carbon treatments (SHIRASAGI ® DC-32) | 0.25 |
| 17CX01.HQ00029 | 1 Granular carbon treatments (SHIRASAGI ® DC-32) | 0.32 |

SBE$_{6.6}$-β-CD Solution Color Analysis

| SBE$_{6.6}$-β-CD (100 mM) | Carbon Processing Cond. | t = 0 (DE) | t = 7 days @ 60° C. (DE) |
|---|---|---|---|
| 17CX01.HQ00044 | 2 Granular carbon treatments (SHIRASAGI ® DC-32) | 0.08 | 0.01 |
| 17CX01.HQ00037 | 2 Granular carbon treatments (SHIRASAGI ® DC-32) | 0.12 | 0.15 |
| 17CX01.HQ00035 | 2 Granular carbon treatments (SHIRASAGI ® DC-32) | 0.09 | 0.18 |
| 17CX01.HQ00033 | 1 Granular carbon treatments (SHIRASAGI ® DC-32) | 0.2 | 0.41 |
| 17CX01.HQ00029 | 1 Granular carbon treatments (SHIRASAGI ® DC-32) | 0.12 | 0.38 |

L = lightness; 100 for perfect white and 0 for black;
a = measures redness when positive, grey when zero, and greeness when negative;
b = measures yellowness when positive, grey when zero, and blueness when negative;
DE = Total Differences $\sqrt{(\Delta L^2 + \Delta a^2 + \Delta b^2)}$ from the Standard Triazole API/SBE$_{6.6}$-β-CD Solution Color Analysis

| Formulation | UV/Vis Analysis (DE) | |
|---|---|---|
| | t = 0 (DE) | t = 7 days @ 60° C. (DE) |
| 17CX01.HQ00044 | 0.46 | 4.37 |
| 17CX01.HQ00037 | 0.2 | 3.76 |
| 17CX01.HQ00035 | 0.24 | 4.43 |
| 17CX01.HQ00033 | 0.45 | 5 |
| 17CX01.HQ00029 | 0.36 | 6.26 |

L = lightness; 100 for perfect white and 0 for black;
a = measures redness when positive, grey when zero, and greeness when negative;
b = measures yellowness when positive, grey when zero, and blueness when negative;
DE = Total Differences $\sqrt{(\Delta L^2 + \Delta a^2 + \Delta b^2)}$ from the Standard.

Triazole API/SBE$_{6.6}$-β-CD—Triazole API Assay Analysis

| SBE$_{6.6}$-β-CD Lot No. | Triazole API Assay | | |
|---|---|---|---|
| | t = 0 | t = 7 days @ 60° C. | Δ Assay (t = 0→t = 7 days) |
| 17CX01.HQ00044 | 99.94% | 99.80 | 0.14 |
| 17CX01.HQ00037 | 99.98% | 99.61 | 0.36 |
| 17CX01.HQ00035 | 99.97% | 99.60 | 0.37 |
| 17CX01.HQ00033 | 99.96% | 99.60 | 0.36 |
| 17CX01.HQ00029 | 99.95% | 99.57 | 0.38 |

The UV analysis demonstrated that the UV-active impurities present in the initial SBE$_{6.6}$-β-CD composition are much lower when a the cyclodextrin composition is treated twice with activated carbon. The Hunter color analysis of the SBE$_{6.6}$-β-CD composition alone, as well as the triazole API/SBE$_{6.6}$-β-CD formulation samples indicated lower DE values for those SBE$_{6.6}$-β-CD lots that were processed using a double activated carbon treatment. There was little difference between the triazole API assay content before and after the 7 day-60° C. stress test. Thus, the lower impurity levels in the SBE$_{6.6}$-β-CD composition that was treated twice with activated carbon results in less a reduced level of triazole API degradation, as well as reduced formation of color-forming agents.

Example 33

SBE$_{6.6}$-β-CD DS Subjected to Heat then Carbon Treatment

The effect of heating a derivatized cyclodextrin composition of the present invention was studied as follows. The SBE$_{6.6}$-β-CD composition prepared according to Example 22 was dissolved in aqueous solution and analyzed using UV/vis spectrophotometry. Specifically, a 30% w/w β-cyclodextrin solution was prepared by dissolving 70 grams of SBE$_{6.6}$-β-CD Lot No. 17CX01.HQ00044 (corrected for water content) in 230 mL of water. This initial solution was analyzed on a PERKIN ELMER Lambda 35 UV/Vis spectrophotometer, scanning from 190 nm to 400 nm at a speed of 240 nm/min and a slit width of 1.0 nm. The sample was blanked against water before analysis. The solution was heated with agitation to 70° C. for 48 hours. The solution was cooled to ambient temperature and divided. To each of the divided solutions, pre-washed SHIRASAGI® DC32 granular activated carbon was added. The SBE$_{6.6}$-β-CD solutions were stirred for 3 hours, and then the activated carbon was filtered using a 0.22 μm PVDF filter. The solutions were analyzed using a PERKIN ELMER Lambda 35 UV/Vis spectrophotometer, scanning from 190 nm to 400 nm at a speed of 240 nm/min and a slit width of 1.0 nm. The samples were blanked against water before analysis.

Figure 4:
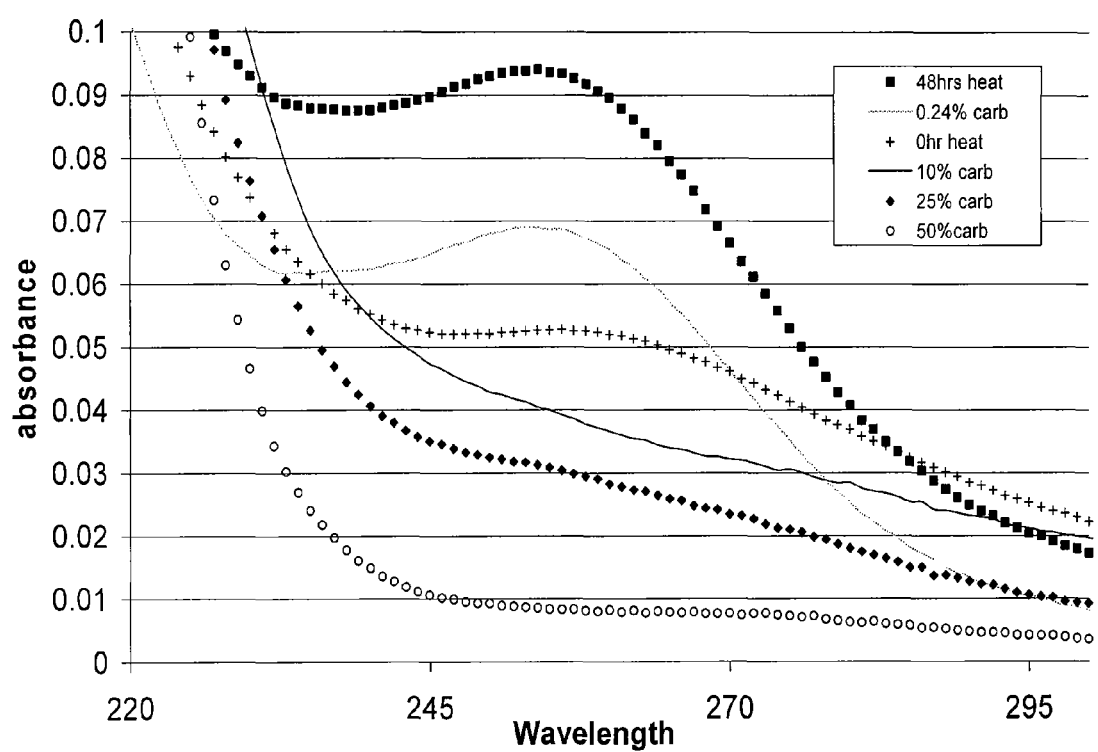
FIG. 4 provides a graphic representation of a UV scan (190 nm to 400 nm) of a solution containing a SAE-β-CD after exposure to a temperature of 70° C. for a period of 48 hours, with subsequent treatment with varying amounts of activated carbon.

The data is depicted graphically in FIG. 4. Referring to FIG. 4, the UV/vis absorption of the solution prior to heat treatment (++++), immediately after 48 hours of heat treatment (■■■■), and after exposure to activated carbon at a loading of 0.24% w/w (●●●●●●●●), 10% w/w (—), 25% w/w (♦♦♦♦), and 50% w/w (○○○○), (according to the concentration of SBE$_{6.6}$-β-CD), is provided. The data shows that exposing the SBE$_{6.6}$-β-CD solution to heat for 48 hours resulted in a significant increase (approximately 95%) in the absorption maximum at a wavelength of 245 nm to 270 nm. However, treatment with activated carbon decreases the absorption in this wavelength range. Thus, the drug-degrading impurity having an absorption at a wavelength of 245 nm to 270 nm increases with heating, but can be removed through carbon treatment.

Example 34

SBE$_{6.6}$-β-CD DS and API Stability

Comparative evaluation of various lots of SBE$_{6.6}$-β-CD processed with a single or a double carbon treatment with an antipsychotic API (aripiprazole) were examined by UV/vis spectrophotometry and HPLC analysis. The general procedure used to evaluate the stability of the SBE$_{6.6}$-β-CD/API formulations is provided below.

Aqueous solutions comprising samples of the API (aripiprazole) were prepared with an API concentration of 7.5 mg/mL and a $SBE_{6.6}$-β-CD concentration of 150 mg/mL. Tartaric acid was added to water until dissolved, and the $SBE_{6.6}$-β-CD was then added to the tartaric acid solution. The API was then added to the solutions, and dissolved within about 10 minutes of the additions. The mixture was stirred about 1 hour, heated treated, and then filtered through a sterile filter. This process was performed using the following lots of $SBE_{6.6}$-β-CD, some of which underwent a single treatment with activated carbon and others that underwent two treatments with activated carbon ($SBE_{6.6}$-β-CD Lot Nos. 17CX01.HQ00021, 17CX01.HQ00025, 17CX01.HQ00029, 17CX01.HQ00035, 17CX01.HQ00036, 17CX01.HQ00037, 17CX01.HQ00038, 17CX01.HQ00039, 17CX01.HQ00040, 17CX01.HQ00041, 17CX01.HQ00042, 17CX01.HQ00043 and 17CX01.HQ00044). Solution samples were placed in a stability chamber at 50° C. for up to 9 weeks. Samples were removed at 4 weeks and again at 9 weeks, and HPLC analysis was performed to determine the extent of API degradation.

Aqueous solution_samples were analyzed by UV/vis spectrophotometry using the following procedure. A 30% w/w β-cyclodextrin solution was prepared by dissolving of the above $SBE_{6.6}$-β-CD lots (corrected for water content) in water. The solution was analyzed in a 1 cm cuvette using a PERKIN ELMER Lambda 35 UV/Vis spectrophotometer, scanning from 190 nm to 400 nm at a speed of 240 nm/min and a slit width of 1.0 nm. The samples were blanked against water before analysis. The following tables include the data from this study.

$SBE_{6.6}$-β-CD Lot Summary and UV Content

| 30% $SBE_{6.6}$-β-CD Solutions Lots | # of Carbon Treatments | SAE-CD UV Analysis (Max Abs @ λ = 245-270 nm) |
|---|---|---|
| 17CX01.HQ00021 | 1 | 0.21 |
| 17CX01.HQ00025 | 1 | 0.44 |
| 17CX01.HQ00029 | 1 | 0.21 |
| 17CX01.HQ00035 | 2 | 0.16 |
| 17CX01.HQ00036 | 2 | 0.14 |
| 17CX01.HQ00037 | 2 | 0.15 |
| 17CX01.HQ00038 | 2 | 0.1 |
| 17CX01.HQ00039 | 2 | 0.09 |
| 17CX01.HQ00040 | 2 | 0.09 |
| 17CX01.HQ00041 | 2 | 0.08 |
| 17CX01.HQ00042 | 2 | 0.07 |
| 17CX01.HQ00043 | 2 | 0.1 |
| 17CX01.HQ00044 | 2 | 0.05 |

SAE-CD & API Impurity Analysis

| $SBE_{6.6}$-β-CD (150 mg/mL) API (7.5 mg/mL) | t = 0 | t = 4 wks @ 50° C. | Δ Assay (t = 0→t = 4 wks) | t = 9 wks @ 50° C. | Δ Assay (t = 0→t = 9 wks) |
|---|---|---|---|---|---|
| 17CX01.HQ00021 | 0.05 | 0.90 | 0.85 | 1.24 | 1.19 |
| 17CX01.HQ00025 | 0.00 | 1.08 | 1.08 | 1.42 | 1.42 |
| 17CX01.HQ00029 | 0.23 | 1.04 | 0.81 | 1.52 | 1.29 |
| 17CX01.HQ00035 | 0.08 | 0.63 | 0.55 | 0.96 | 0.88 |
| 17CX01.HQ00036 | 0.08 | 0.58 | 0.50 | 0.87 | 0.79 |
| 17CX01.HQ00037 | 0.08 | 0.65 | 0.57 | 0.85 | 0.77 |
| 17CX01.HQ00038 | 0.07 | 0.52 | 0.45 | 0.78 | 0.71 |
| 17CX01.HQ00039 | 0.07 | 0.55 | 0.48 | 0.86 | 0.79 |
| 17CX01.HQ00040 | 0.00 | 0.21 | 0.21 | 0.53 | 0.53 |
| 17CX01.HQ00041 | 0.00 | 0.27 | 0.27 | 0.51 | 0.51 |
| 17CX01.HQ00042 | 0.00 | 0.34 | 0.34 | 0.64 | 0.64 |
| 17CX01.HQ00043 | 0.07 | 0.61 | 0.54 | 1.00 | 0.93 |
| 17CX01.HQ00044 | 0.00 | 0.13 | 0.13 | 0.35 | 0.35 |

The data shows that the API undergoes significantly higher degradation when it is formulated with an $SBE_{6.6}$-β-CD lot that has undergone only a single treatment with activated carbon. The API formulation that contained $SBE_{6.6}$-β-CD Lot No. 17CX01.HQ00025 had the highest UV-active impurity levels (Max. Abs.=0.44 A.U.) and the API underwent a total degradation of 1.42% after 9 weeks. $SBE_{6.6}$-β-CD lots that underwent two treatments with activated carbon were measurably lower in terms of both levels of UV-active impurities and the extent of API degradation. The extent of API degradation that occurred during storage for 9 weeks at 50° C. correlated with the concentration of UV-active impurities present in the formulations. For example, the API formulation containing $SBE_{6.6}$-β-CD Lot No. 17CX01.HQ00044 (which contained UV-active impurities having a Max. Abs.=0.05 A.U.) underwent a total degradation of only 0.35% after 9 weeks at 50° C.

Figure 5:
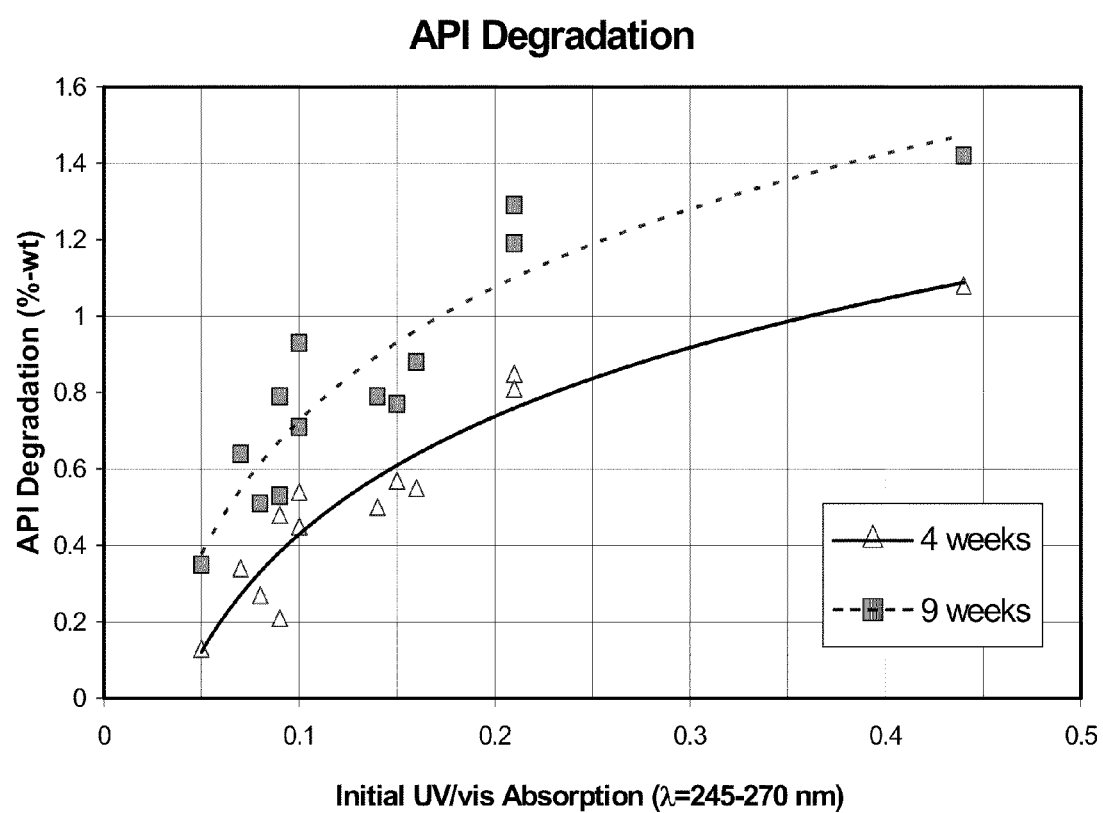
FIG. 5 provides a graphic representation of the effect of initial UV/Vis absorption of a $SBE_{6.6}$-β-CD solution on API stability.

FIG. 5 provides a graphical representation of the correlation between the initial UV/vis absorption of the $SBE_{6.6}$-β-CD lots at a wavelength of 245 nm to 270 nm, and the extent of API degradation determined at 4 weeks and 9 weeks. Referring to FIG. 5, the data shows that at both 4 weeks (——△——) and 9 weeks (- -■- -) that the extent of the API degradation increases with the concentration of the UV/vis absorbing drug-degrading impurities present in the $SBE_{6.6}$-β-CD composition.

CONCLUSION

These examples illustrate possible embodiments of the present invention. While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections can set forth one or more, but not all exemplary embodiments of the present invention as contemplated by the inventor(s), and thus, are not intended to limit the present invention and the appended claims in any way.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A sulfoalkyl ether cyclodextrin (SAE-CD) composition comprising a sulfoalkyl ether cyclodextrin having an average degree of substitution of 4.5 to 7.5 and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

2. A SAE-CD composition comprising a sulfoalkyl ether cyclodextrin having an average degree of substitution of 4.5 to 7.5 and less than 100 ppm of a phosphate, wherein the SAE-CD composition has an absorption of less than 0.5 A.U. due to a drug-degrading agent, as determined by UV/vis spectrophotometry at a wavelength of 245 nm to 270 nm for an aqueous solution containing 500 mg of the SAE-CD composition per mL of solution in a cell having a 1 cm path length.

3. A SAE-CD composition comprising a sulfoalkyl ether cyclodextrin and less than 100 ppm of a phosphate, wherein the sulfoalkyl ether cyclodextrin is sulfobutyl ether cyclodextrin, and wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

4. A SAE-CD composition comprising a sulfoalkyl ether cyclodextrin and less than 100 ppm of a phosphate, wherein the sulfoalkyl ether cyclodextrin is sulfobutyl ether cyclodextrin, and wherein the SAE-CD composition has an absorption of less than 0.5 A.U. due to a drug-degrading agent, as determined by UV/vis spectrophotometry at a wavelength of 245 nm to 270 nm for an aqueous solution containing 500 mg of the SAE-CD composition per mL of solution in a cell having a 1 cm path length.

5. The SAE-CD composition of any of claims 1-4, wherein the SAE-CD composition has an absorption of less than 0.2 A.U. due to the drug-degrading agent as determined by UV/vis spectrophotometry at a wavelength of 245 nm to 270 nm.

6. The SAE-CD composition of any of claims 1-4, wherein the SAE-CD composition has an absorption of less than 0.2 A.U., due to a color-forming agent, as determined by UV/vis spectrophotometry at a wavelength of 320 nm to 350 nm for an aqueous solution containing 500 mg of the SAE-CD composition per mL of solution in a cell having a 1 cm path length.

7. The SAE-CD composition of any of claims 1-4, wherein the SAE-CD composition further comprises:
less than 20 ppm of a sulfoalkylating agent;
less than 0.5% wt. of an underivatized cyclodextrin;
less than 1% wt. of an alkali metal halide salt; and
less than 0.25% wt. of a hydrolyzed sulfoalkylating agent.

8. The SAE-CD composition of any of claims 1-4, wherein the sulfoalkyl ether cyclodextrin is a compound of Formula (1):

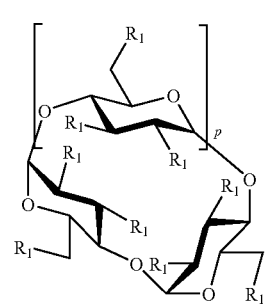

Formula (1)

wherein p is 4, 5 or 6, and $R_1$ is independently selected at each occurrence from —OH or —O—($C_2$-$C_6$ alkylene)-$SO_3^-$-T, wherein T is independently selected at each occurrence from pharmaceutically acceptable cations, provided that at least one $R_1$ is —OH and at least one $R_1$ is —O—($C_2$-$C_6$ alkylene)-$SO_3^-$-T.

9. The SAE-CD composition of claim 8, wherein $R_1$ is independently selected at each occurrence from —OH or —O—($C_4$ alkylene)-$SO_3^-$-T, and -T is $Na^+$ at each occurrence.

10. The SAE-CD composition of claim 8, wherein the pharmaceutically acceptable cation is: $H^+$, an alkali metal cation, an alkaline earth metal cation, an ammonium ion, or an amine cation.

11. The SAE-CD composition of claim 10, wherein the pharmaceutically acceptable cation is an alkali metal cation which is $Li^+$, $Na^+$, or $K^+$.

12. The SAE-CD composition of claim 10, wherein the pharmaceutically acceptable cation is an alkaline earth metal cation which is $Ca^{2+}$ or $Mg^{2+}$.

13. The SAE-CD composition of claim 10, wherein the pharmaceutically acceptable cation is an amine cation which is the cation of: (C1-C6)-alkylamine, piperidine, pyrazine, (C1-C6) alkanolamine, ethylenediamine, or (C4-C8)-cycloalkanolamine.

14. The SAE-CD composition of any of claims 1-4, wherein the SAE-CD composition comprises:
less than 50 ppm of a phosphate;
less than 10 ppm of a sulfoalkylating agent;
less than 0.2% wt. of an underivatized cyclodextrin;
less than 0.5% wt. of an alkali metal halide salt; and
less than 0.1% wt. of a hydrolyzed sulfoalkylating agent;
wherein the SAE-CD composition has an absorption of
less than 0.2 A.U., due to a color-forming agent, as determined by UV/vis spectrophotometry at a wavelength of 320 nm to 350 nm for an aqueous solution containing 500 mg of the SAE-CD composition per mL of solution in a cell having a 1 cm path length.

15. The SAE-CD composition of any of claims 1-4, wherein the SAE-CD composition comprises:
less than 10 ppm of a phosphate;
less than 2 ppm of a sulfoalkylating agent;
less than 0.1% wt. of an underivatized cyclodextrin;
less than 0.2% wt. of an alkali metal halide salt; and
less than 0.08% wt. of a hydrolyzed sulfoalkylating agent;
wherein the SAE-CD composition has an absorption of
less than 0.1 A.U., due to a color-forming agent, as determined by UV/vis spectrophotometry at a wavelength of 320 nm to 350 nm for an aqueous solution containing 500 mg of the SAE-CD composition per mL of solution in a cell having a 1 cm path length.

16. The SAE-CD composition of any of claims 1-4, wherein the SAE-CD composition comprises:
  less than 5 ppm of a phosphate;
  less than 250 ppb of a sulfoalkylating agent;
  less than 0.1% wt. of an underivatized cyclodextrin;
  less than 0.05% wt. of an alkali metal halide salt; and
  less than 0.08% wt. of a hydrolyzed sulfoalkylating agent.

17. The SAE-CD composition of any of claims 1-4, wherein the average degree of substitution of the SAE-CD is 6 to 7.1.

18. The SAE-CD composition of claim 17, wherein the average degree of substitution of the SAE-CD is 6.5 to 7.

19. A sulfoalkyl ether cyclodextrin (SAE-CD) composition comprising a sulfobutyl ether cyclodextrin having an average degree of substitution of 6 to 7.1 and less than 100 ppm of a phosphate, wherein the SAE-CD composition has an absorption of less than 0.2 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

20. A sulfoalkyl ether cyclodextrin (SAE-CD) composition comprising a sulfobutyl ether cyclodextrin having an average degree of substitution of 6 to 7.1 and less than 100 ppm of a phosphate, wherein the SAE-CD composition has an absorption of less than 0.2 A.U. due to a drug-degrading agent, as determined by UV/vis spectrophotometry at a wavelength of 245 nm to 270 nm for an aqueous solution containing 500 mg of the SAE-CD composition per mL of solution in a cell having a 1 cm path length.

21. A SAE-CD composition produced by a process comprising:
  (a) mixing in an aqueous medium a cyclodextrin with a sulfoalkylating agent in the presence of an alkalizing agent to form an aqueous reaction milieu comprising a sulfoalkyl ether cyclodextrin, one or more unwanted components, and one or more drug-degrading impurities;
  (b) conducting one or more separations to remove the one or more unwanted components from the aqueous milieu to form a partially purified aqueous solution comprising the sulfoalkyl ether cyclodextrin and the one or more drug-degrading impurities, wherein the one or more separations include a process selected from the group consisting of: ultrafiltration, diafiltration, centrifugation, extraction, solvent precipitation, and dialysis; and
  (c) treating the partially purified aqueous solution with a phosphate-free activated carbon two or more times to provide the SAE-CD composition, wherein the SAE-CD composition has an absorption of less than 0.5 A.U. due to a drug-degrading agent, as determined by UV/vis spectrophotometry at a wavelength of 245 nm to 270 nm for an aqueous solution containing 300 mg of the SAE-CD composition per mL of solution in a cell having a 1 cm path length.

22. The SAE-CD composition of claim 21, wherein the treating comprises:
  adding a phosphate-free particulate or powdered activated carbon to the partially purified aqueous solution while mixing, separating the activated carbon from the solution, and repeating the adding and the separating at least once until the amount of drug-degrading agent in the solution is reduced to a target level; or
  passing and recycling the partially purified aqueous solution through a mass of phosphate-free activated carbon in a flow-through apparatus until the amount of drug-degrading agent in the solution is reduced to a target level.

23. The SAE-CD composition of claim 22, wherein the treating comprises passing and recycling the partially purified aqueous solution through the mass of phosphate-free activated carbon two or more times, wherein each passing is with a different mass of phosphate-free activated carbon.

24. The SAE-CD composition of claim 23, wherein the activated carbon present during, the treating is about 12% by weight of the sulfoalkyl ether cyclodextrin, and the treating is performed for at least 2 hours.

25. The SAE-CD composition of claim 21, wherein the weight ratio of the SAE-CD to the activated carbon is 8.3:1 to 8.5:1.

26. The SAE-CD composition of claim 21, wherein the composition is produced by a process further comprising degrading excess sulfoalkylating agent by exposing the reaction milieu to a temperature of 60° C. to 80° C. for 6 hours to 72 hours.

27. The SAE-CD composition of claim 21, wherein the composition is produced by a process further comprising degrading excess sulfoalkylating agent by exposing the reaction milieu to a temperature of 75° C. to 80° C. for 6 hours to 72 hours.

28. The SAE-CD composition of claim 21, wherein the one or more separations include ultrafiltration with a molecular weight cutoff of about 1,000 Da.

29. A composition comprising the SAE-CD composition of claim 1 and an excipient.

30. The composition of claim 29, further comprising an active agent.

31. The composition of claim 30, wherein the composition is a pharmaceutical composition.

32. A composition comprising the SAE-CD composition of claim 1 and an active agent.

33. The composition of claim 32, wherein the composition is a pharmaceutical composition.

34. A composition comprising the SAE-CD composition of claim 2 and an excipient.

35. The composition of claim 34, further comprising an active agent.

36. The composition of claim 35, wherein the composition is a pharmaceutical composition.

37. A composition comprising the SAE-CD composition of claim 2 and an active agent.

38. The composition of claim 37, wherein the composition is a pharmaceutical composition.

39. A composition comprising the SAE-CD composition of claim 3 and an excipient.

40. The composition of claim 39, further comprising an active agent.

41. The composition of claim 40, wherein the composition is a pharmaceutical composition.

42. A composition comprising the SAE-CD composition of claim 3 and an active agent.

43. The composition of claim 42, wherein the composition is a pharmaceutical composition.

44. A composition comprising the SAE-CD composition of claim 4 and an excipient.

45. The composition of claim 44, further comprising an active agent.

46. The composition of claim 45, wherein the composition is a pharmaceutical composition.

47. A composition comprising the SAE-CD composition of claim 4 and an active agent.

48. The composition of claim 47, wherein the composition is a pharmaceutical composition.

49. A composition comprising the SAE-CD composition of claim 19 and an excipient.

50. The composition of claim 49, further comprising an active agent.

51. The composition of claim 50, wherein the composition is a pharmaceutical composition.

52. A composition comprising the SAE-CD composition of claim 19 and an active agent.

53. The composition of claim 52, wherein the composition is a pharmaceutical composition.

54. A composition comprising the SAE-CD composition of claim 20 and an excipient.

55. The composition of claim 54, further comprising an active agent.

56. The composition of claim 55, wherein the composition is a pharmaceutical composition.

57. A composition comprising the SAE-CD composition of claim 20 and an active agent.

58. The composition of claim 57, wherein the composition is a pharmaceutical composition.

59. A composition comprising the SAE-CD composition of claim 21 and an excipient.

60. The composition of claim 59, further comprising an active agent.

61. The composition of claim 60, wherein the composition is a pharmaceutical composition.

62. A composition comprising the SAE-CD composition of claim 21 and an active agent.

63. The composition of claim 62, wherein the composition is a pharmaceutical composition.

64. A SAE-CD composition produced by a process comprising:
(a) mixing in an aqueous medium a cyclodextrin with a sulfoalkylating agent in the presence of an alkalizing agent to form an aqueous reaction milieu comprising a sulfoalkyl ether cyclodextrin, one or more unwanted components, and one or more drug-degrading impurities;
(b) conducting one or more separations to remove the one or more unwanted components from the aqueous milieu to form a partially purified aqueous solution comprising the sulfoalkyl ether cyclodextrin and the one or more drug-degrading impurities, wherein the one or more separations include a process selected from the group consisting of: ultrafiltration, diafiltration, centrifugation, extraction, solvent precipitation, and dialysis; and
(c) treating the partially purified aqueous solution with a phosphate-free activated carbon two or more times to provide the SAE-CD composition, wherein the SAE-CD composition has an absorption of less than 0.5 A.U. due to a drug-degrading agent, as determined by UV/vis spectrophotometry at a wavelength of 245 nm to 270 nm for an aqueous solution containing 500 mg of the SAE-CD composition per mL of solution in a cell having a 1 cm path length.

65. The SAE-CD composition of claim 64, wherein the treating comprises:
adding a phosphate-free particulate or powdered activated carbon to the partially purified aqueous solution while mixing, separating the activated carbon from the solution, and repeating the adding and the separating at least once until the amount of drug-degrading agent in the solution is reduced to a target level; or
passing and recycling the partially purified aqueous solution through a mass of phosphate-free activated carbon in a flow-through apparatus until the amount of drug-degrading agent in the solution is reduced to a target level.

66. The SAE-CD composition of claim 65, wherein the treating comprises passing and recycling the partially purified aqueous solution through the mass of phosphate-free activated carbon two or more times, wherein each passing is with a different mass of phosphate-free activated carbon.

67. The SAE-CD composition of claim 66, wherein the activated carbon present during the treating is about 12% by weight of the sulfoalkyl ether cyclodextrin, and the treating is performed for at least 2 hours.

68. The SAE-CD composition of claim 64, wherein the weight ratio of the SAE-CD to the activated carbon is 8.3:1 to 8.5:1.

69. The SAE-CD composition of claim 64, wherein the composition is produced by a process further comprising degrading excess sulfoalkylating agent by exposing the reaction milieu to a temperature of 60° C. to 80° C. for 6 hours to 72 hours.

70. The SAE-CD composition of claim 64, wherein the composition is produced by a process further comprising degrading excess sulfoalkylating agent by exposing the reaction milieu to a temperature of 75° C. to 80° C. for 6 hours to 72 hours.

71. The SAE-CD composition of claim 64, wherein the one or more separations include ultrafiltration with a molecular weight cutoff of about 1,000 Da.

72. A composition comprising the SAE-CD composition of claim 64 and an excipient.

73. The composition of claim 72, further comprising an active agent.

74. The composition of claim 73, wherein the composition is a pharmaceutical composition.

75. A composition comprising the SAE-CD composition of claim 64 and an active agent.

76. The composition of claim 75, wherein the composition is a pharmaceutical composition.

* * * * *

UNITED STATES PATENT AND TRADEMARK OFFICE
CERTIFICATE OF CORRECTION

PATENT NO. : 8,410,077 B2  
APPLICATION NO. : 12/613103  
DATED : April 2, 2013  
INVENTOR(S) : Vincent D. Antle It is certified that error appears in the above-identified patent and that said Letters Patent is hereby corrected as shown below:

On the Title Page

In column 2 (page 1 item 56) at line 45, Under Other Publications, change "Derivatives,Their" to --Derivatives, Their--.

In the Specification

In column 2 at line 3, Change "Tray." to --trav--.

In column 12 at line 25, Change "wherein:p" to --wherein: p--.

In column 15 at line 67, Change "derivative" to --derivative.--.

In column 23 at line 26, Change "Antifunal" to --Antifungal--.

In column 23 at line 30, Change "tetconazole," to --terconazole,--.

In column 23 at line 36, Change "ziprasidone" to --ziprasidone.--.

In column 23 at line 56, Change "normarcotic" to --nonnarcotic--.

In column 23 at line 59, Change "normarcotic" to --nonnarcotic--.

In column 23 at line 67, Change "disulfuram," to --disulfiram,--.

In column 24 at line 15, Change "oxalodinones," to --oxazolidinones,--.

In column 29 at line 37, Change "5203;" to --S203;--.

In column 29 at line 37, Change "Opthalmol." to --Ophthalmol.--.

In column 30 at line 66, Change "acetyltryptophonate," to --acetyltryptophanate--.

In column 31 at lines 56-57, Change "poloxomers," to --poloxamers,--.

In column 32 at line 64, Change "the a" to --the--.

In column 38 at lines 65-66, Change "bis(4-sulfobutyl)eEther," to --bis(4-sulfobutyl)$_e$Ether,--.

In column 42 at line 35, Change "Fullereton," to --Fullerton,--.

In column 50 at line 1, Change "a the" to --the--.

Signed and Sealed this  
Third Day of June, 2014

Michelle K. Lee  
*Deputy Director of the United States Patent and Trademark Office*

CERTIFICATE OF CORRECTION (continued)
U.S. Pat. No. 8,410,077 B2

In the Claims

In column 54 at line 23 (approx.), In Claim 9, change "–($C_4$alkylene)-" to -- –($C_4$ alkylene)- --.

In column 56 at line 10 (approx.), In Claim 24, change "during," to --during- --.